(12) United States Patent
Chen et al.

(10) Patent No.: US 7,939,058 B2
(45) Date of Patent: May 10, 2011

(54) USES OF IL-12 IN HEMATOPOIESIS

(75) Inventors: Tingchao Chen, Monterey Park, CA (US); Yi Zhao, South Pasadena, CA (US); W. French Anderson, San Marino, CA (US)

(73) Assignee: University of Southern California, Los Angeles, CA (US)

( * ) Notice: Subject to any disclaimer, the term of this patent is extended or adjusted under 35 U.S.C. 154(b) by 746 days.

(21) Appl. No.: 10/886,267

(22) Filed: Jul. 6, 2004

(65) Prior Publication Data

US 2005/0136034 A1    Jun. 23, 2005

Related U.S. Application Data

(60) Provisional application No. 60/485,170, filed on Jul. 3, 2003.

(51) Int. Cl.
  *A61K 38/19* (2006.01)
  *C07K 14/52* (2006.01)
(52) U.S. Cl. ........ 424/85.2; 514/7.9; 514/19.2; 530/351
(58) Field of Classification Search .................. None
  See application file for complete search history.

(56) References Cited

U.S. PATENT DOCUMENTS

| 6,080,399 A * | 6/2000 | Gajewski et al. ............ 424/85.2 |
| 6,423,308 B1 * | 7/2002 | Yarchoan et al. ............ 424/85.2 |

OTHER PUBLICATIONS

Muraro et al., Neurotherapeutics, 2007, 4(4):676-92.*
Androulakis et al., Eur. J. Cancer, 2002, 38(15):1992-1997.*
Tsung et al., J. immunol., 1998, vol. 160:1369-1377.*
Maestroni et al., Cancer Res., 1994, vol. 54:2429-2432.*
Hawkins et al., Cancer, 2002, vol. 95:1354-1365.*
Teicher et al., Clin. Cancer Res., 1997, vol. 3(9):1661-1667.*
Motzer et al., Clin. Cancer Res., 1998, vol. 4:1183-1192.*
Neta, R. et al., "IL-12 Protects Bone Marrow from and Sensitizes Intestinal Tract to Ionizing Radiation." The Journal of Immunology, 1994, 153:4230-4237.*
Wang, Y. et al., "The Effect of Interleukin (IL) 12 on Hemopoiesis in Irradiated Mice," Nat'l Med. J. China, Mar. 1997, 77(3):216-219.*
Xia, D. et al., Study on the Antitumor Activity of CBMC Activated by IL-12 Alone or in Combination with IL-12, China J. Hematol., Jan. 2000, 21(1):30-33.*
Atkins, M.B. et al., "Phase I Evaluation of Intravenous Recombinant Human Interleukin 12 in Patients with Advanced Malignancies," Clinical Cancer Research, Mar. 1997, vol. 3, pp. 409-417.
Basile, L.A. et al., "Multilineage hematopoietic recovery with concomitant antitumor effects using low dose Interleukin-12 in myelosuppressed tumor-bearing mice," Journal of Translational Medicine, May 19, 2008, vol. 6, pp. 1-27.
Chen, T. et al., "IL-12 Facilitates Both the Recovery of Endogenous Hematopoiesis and the Engraftment of Stem Cells after Ionizing Radiation," Experimental Hematology, Feb. 2007, vol. 35, No. 2, pp. 203-213.
Jacobsen, S.E.W. et al., "IL12, a direct stimulator and indirect inhibitor of haematopoiesis," Research in Immunology, Editions Scientifiques Et Medicales Elsevier, Sep. 1, 1995, vol. 146, No. 7-8, pp. 506-514.
Mohan, K. et al., "Interleukin-12 corrects severe anemia during blood-stage Plasmodium chabaudi AS in susceptible A/J mice," Experimental Hematology, 1998, vol. 26, No. 1, pp. 45-52.
Neta, R., "Modulation of Radiation Damage by Cytokines," Stem Cells, 1997, vol. 15, Supp. 2, pp. 87-94.
Supplementary Partial European Search Report for European Pat. App. No. EP04777663, dated Oct. 14, 2008, 9 pages.
Car, Bruce D. et al., "The Toxicology of Interleukinn-12: A Review," Toxicologic Pathology, (1999), vol. 27, No. 1, pp. 58-63.
White, S. C. et al., "Phase II Study of Oral Topotecan in Advanced Non-Small Cell Lung Cancer," Clinical Cancer Research, (Mar. 2000) 6:868-873.
Reni, M. et al., "Definitive Results of a Phase II Trial of Cisplatin, Epirubicin, Continuous-Infusion Fluorouracil, and Gemcitabine in Stage IV Pancreatic Adenocarcinoma," Journal of Clinical Oncology (May 15, 2001) (19)10:2679-2686.
Cadron, I. et al., "The "Leuven" dose-dense paclitaxel/carboplatin regimen in patients with recurrent ovarian cancer," (2007) Gynecologic Oncology, 106:354-361.
FDA—Public Health Advisory, "Safety" Erythropoiesis Stimulating Agents: Aranesp (darbepoetin alfa), Epogen (epoetin alfa), and Procrit (epoetin alfa) (Mar. 7, 2008)
Amgen Inc., "Epogeno® (Epoetin alfa) for Injection" Amgen Inc. (Revised: Apr. 2009) 1-31, 1xxxxxx—v21.
Leyland-Jones, B. et al., "Maintaining Normal Hemoglobin Levels With Epoetin Alfa in Mainly Nonanemic Patients With Metastatic Breast Cancer Receiving First-Line Chemotherapy: A Survival Study," J Clin Oncol, (Sep. 1, 2005) 23:5960-5972.
Wright, J. R. et al., "Randomized, Double-Blind, Placebo-Controlled Trial of Erythropoietin in Non-Small-Cell Lung Cancer With Disease-Related Anemia," J of Clinical Oncology, (Mar. 20, 2007) (25)9:1027-1032.
Gutschalk, C.M.,et al., "Granulocyte Colony-Stimulating Factor and Granulocyte-Macrophage Colony-Stimulating Factor Promote Malignant Growth of Cells from Head and Neck Squamous Cell Carcinomas In vivo," (2006) Cancer Res. (66)16:8026-36.
Okazaki, T. et al., "Granulocyte colony-stimulating factor promotes tumor angiogenesis via increasing circulation endothelial progenitor cells and Gr1 + CD11b + cells in cancer animal modes," Internal Immunology, (2005) (18)1:1-9.

(Continued)

Primary Examiner — Elizabeth C. Kemmerer
Assistant Examiner — Xiaozhen Xie
(74) Attorney, Agent, or Firm — Foley & Lardner LLP

(57) ABSTRACT

Methods for enhancing or stimulating hematopoiesis including the step of administering Interleukin-12 (IL-12) to yield hematopoietic recovery in a mammal in need. Preferred methods include the step of administering IL-12 as an adjuvant therapy to alleviate the hematopoietic toxicities associated with one or more treatment regimens used to combat a disease state. Other methods include administering IL-12 to ameliorate various hematopoietic deficiencies. Still other methods are directed to uses of IL-12 for in-vivo proliferation of hematopoietic repopulating cells, hematopoietic progenitor cells and hematopoietic stem cells. Other disclosed methods are directed to uses of Il-12 for bone marrow preservation or recovery.

15 Claims, 19 Drawing Sheets

OTHER PUBLICATIONS

Wyeth Pharmaceuticals— Package Insert, "Neumega® (oprelvekin)"; Revised Mar. 2009, Product Information of Wyeth Pharmaceuticals, Inc.; pp. 1-27.

Oudard, S. "Treatment options in renal cell carcinoma: past, present and future," *Annals of Oncology* (Sep. 2007) (18)10:x25—x31.

Zagozdzon et al., Effective Chemo-Immunotherapy of L1210 Leukemia in Vivo Using Interleukin-12 Combined with Doxorubicin but not with CycloPhosphamide, Pacitaxel or Cisplatin. Int. J. Cancer 1998, vol. 77, pp. 720-727.

Teicher et al., Optimal Scheduling of Interleukin-12 and Fractionated Radiation Therapy in the Murine Lewis Lung Carcinoma. Radiation Oncology Investigations 1998, vol. 6, pp. 71-80.

Jackson et al., Interleukin-12 Enhances Peripheral Hematopoiesis in Vivo, Blood, vol. 85, No. 9, pp. 2371-2376, (1995).

Ohno et al. A Dose-Escalation and Pharmacokinetic Study of Subcutaneously Administered Recombinant Human Interleukin 12 and Its Biological Effects in Japanese Patients with Advanced Malignancies. Clinical Cancer Research 2000, vol. 6, pp. 2661-2669.

* cited by examiner p value compared with control

| WBC | Day5 | Day8 | Day 12 | Day15 | Day21 | Day28 | Day60 |
|---|---|---|---|---|---|---|---|
| before IR | 0.20 | 0.40 | 0.30 | 0.02 | 0.40 | 0.02 | 0.10 |
| after IR | 0.005 | 0.5 | 0.5 | 0.2 | 0.08 | 0.2 | 0.2 |

| p value compared with control | | | | | | | |
|---|---|---|---|---|---|---|---|
| RBC | Day5 | Day 8 | Day12 | Day15 | Day21 | Day28 | Day60 |
| before IR | 0.047 | 0.01 | 0.20 | 0.20 | 0.40 | 0.03 | 0.0005 |
| after IR | 0.4 | 0.009 | 0.1 | 0.02 | 0.30 | 0.4 | 0.03 | p value compared with control

| Platelet | Day5 | Day 8 | Day 12 | Day15 | Day21 | Day28 | Day60 |
|---|---|---|---|---|---|---|---|
| before IR | 0.0005 | 0.09 | 0.003 | 0.80 | 0.20 | 0.30 | 0.5 |
| after IR | 0.08 | 0.1 | 0.03 | 0.03 | 0.98 | 0.5 | 0.1 |

| lymphocyte | Day5 | Day8 | Day 12 | Day15 | Day21 | Day28 | Day60 |
| --- | --- | --- | --- | --- | --- | --- | --- |
| before IR | 0.20 | 0.70 | 0.40 | 0.02 | 0.50 | 0.01 | 0.04 |
| after IR | 0.002 | 0.7 | 0.5 | 0.2 | 0.1 | 0.2 | 0.2 | p value compared with control p value compared with control

| neutrophile | Day5 | Day8 | Day 12 | Day15 | Day21 | Day28 | Day60 |
|---|---|---|---|---|---|---|---|
| Before IR | 0.20 | 0.20 | 0.40 | 0.08 | 0.10 | 0.05 | 0.4 |
| After IR | 0.3 | 0.5 | 0.7 | 0.5 | 0.08 | 0.7 | 0.6 |

USES OF IL-12 IN HEMATOPOIESIS

RELATED APPLICATIONS

This application is related to and claims priority from U.S. provisional patent application Ser. No. 60/485,170, filed on Jul. 3, 2003, which is incorporated by reference in its entirety.

BACKGROUND

Many disease states result from insufficient hematopoiesis generally, or insufficient hematopoiesis in one or more blood cell types or blood lineages. Still other disease states result from dysfunction in one or more lineages of the hematopoietic system, such as leukemia. Moreover, many treatments that are given to an individual to combat certain disease states, such as cancer, incidentally decrease the individual's blood supply and/or can lead to bone marrow failure. The toxic hematopoietic side effects of these treatments, therefore, decrease the likelihood of the treatment being successful, and often are the limiting effect that results in cessation of treatment.

Thus, there is a need to develop therapies that can restore hematopoiesis and alleviate hematopoietic deficiencies. Such therapies would be capable of maintaining, stimulating and/ or modulating the blood supply, and also would be useful as an ancillary therapy given to decrease the toxic effects of a primary therapy, such as chemotherapy or radiation therapy.

SUMMARY OF THE INVENTION

The present invention is generally directed to uses of Interleukin-12 (IL-12) in stimulating or enhancing hematopoiesis in a subject in need thereof. In the various embodiments of the invention, the subject is a mammal, and the preferred mammal is a human. The preferred human dosages of IL-12 suitable for use in the various embodiments of the invention range from about 2000 ng/kg to less than about 10 ng/kg, however, dosages of about 1 ng/kg or less may also be suitable in particular therapeutic methods of the present invention.

In the embodiments of the present invention, hematopoiesis can involve in-vivo proliferation or expansion of hematopoietic repopulating cell, hematopoietic stem/progenitor cells or other hematopoietic cells, generally residing in bone marrow, or hematopoiesis can involve protection of hematopoietic repopulating cells, stem/progenitor cells or other hematopoietic cells, generally residing in bone marrow, from chemical and/or radiation injury.

An embodiment of the present invention is directed to methods for treating a disease state in a mammal. The method includes administering a treatment to the mammal that is intended to target the disease state, where the treatment has an associated hematopoietic toxicity, and additionally administering one or more therapeutically effective dose(s) of IL-12 near the time of administration of the treatment, where the administration of IL-12 to the mammal reduces the hematopoietic toxicity of the treatment. Administration of IL-12 in this embodiment of the invention, can take place either before, after or before and after, administration of the treatment intended to target the disease state.

In this embodiment of the present invention, the treatment that is intended to target the disease state is either a form of chemotherapy or radiation therapy, or both. Additionally, the treatment intended to target the disease state generally results in a deficiency in one or more hematopoietic cell types or lineages, which is this embodiment of the invention is ameliorated by administration of IL-12. Moreover, in this embodiment of the invention, high dose treatment modalities, such as near lethal treatment modalities of a chemotherapy and/or radiation therapy, and dose dense treatment regimens can be utilized and more than one type of chemotherapy or radiation therapy can be administered, thus greatly facilitating the eradication or suppression of the disease state. Also in the embodiments of the invention, one or more therapeutically effective dose(s) of IL-12 can administered at various time intervals before, before and after, or after the administration of the treatment.

Various disease states can be treated by this embodiment of the invention. For example, the disease state can be manifested in a form of cancer, where the treatment includes a form of chemotherapy or radiation therapy and is targeted to treating one or more types of solid tumors, such as tumors manifested in breast, lung, prostate, ovarian cancer, or the like. Other forms of cancers that are included in this embodiment of the invention are hematopoietic cell cancers, such as leukemias or lymphomas or the like. In either the case where the disease state is manifested by the presentation of solid tumor or hematopoietic cell disorders (cancers), practicing this method embodiment of the present invention can result in increases rate of remission of the tumors, as compared with administering the treatment modality that is intended to target the disease state alone.

Generally in this embodiment of the invention, the administration of IL-12 results in protection of bone marrow cells from the associated hematopoietic toxicity of the treatment, such as chemoprotection of bone marrow cells when the treatment includes chemotherapy and radioprotection of bone marrow cells when the treatment includes radiation therapy. Further, in this embodiment bone marrow cells can include hematopoietic repopulating cells, hematopoietic stem cells or hematopoeitic progenitor cells.

Another embodiment of the present invention is directed to methods of treating a mammal for a deficiency in hematopoiesis by administering one or more therapeutically effective dose(s) of IL-12 as needed to ameliorate the deficiency. This deficiency in hematopoiesis may be a general deficiency or may include one or more deficiency in specific hematopoietic cell lineages or cell types. In this embodiment of the invention, the deficiency may be exacerbated upon the administration of various forms of chemotherapy or radiation therapy. Moreover, the deficiency may substantially be the result of a disease state that is manifested in the mammal.

In this embodiment, the deficiency is ameliorated by the IL-12 facilitated proliferation of one or more types of bone marrow cells. Further, in this embodiment, the deficiency is preferentially ameliorated by the IL-12 facilitated proliferation of hematopoietic repopulating cells, hematopoietic stem cells or hematopoietic progenitor cells.

In this embodiment of the invention, as stated above, the deficiency may be a general deficiency in hematopoiesis in the mammal, or the deficiency may include a deficiency in one or more specific hematopoietic cell lineages, such as a low white blood cell count, red blood cell count, platelet count, neutrophil count, monocyte count, lymphocyte count, granulocyte count, dendritic cell count, or the like. These deficient states of hematopoiesis may be characterized as a lymphopenia, myelopenia, leukopenia, neutropenia, erythropenia, megakaryopenia, or the like.

Also in this embodiment of the invention, various underlying disease states may be responsible for the hematopoietic deficiency, including various forms of cancer, or other disease states listed in Table I below.

Another embodiment of the present invention is directed to methods of stimulating or enhancing hematopoiesis in a mammal by administering one or more therapeutically effective dose(s) of IL-12 for a duration that is effective to achieve a therapeutic result that includes the stimulation or enhancement of hematopoiesis. In this embodiment, the stimulation or enhancement of hematopoiesis involves the 11-12 facilitated proliferation of bone marrow cells, preferentially, the stimulation or enhancement of hematopoiesis involves the IL-12 facilitated proliferation of hematopoietic repopulating cells, including long-term repopulating cells, hematopoietic progenitor cells or hematopoietic stem cells. Also included in this embodiment are methods that also utilize the administration of radiation therapy and/or chemotherapy.

In this embodiment of the invention, as stated above, the deficiency may be a general deficiency in hematopoiesis in the mammal, or the deficiency may include a deficiency in one or more specific hematopoietic cell lineages, such as a low white blood cell count, red blood cell count, platelet count, neutrophil count, monocyte count, lymphocyte count, granulocyte count, dendritic cell count, or the like. These deficient states of hematopoiesis may be characterized as a lymphopenia, myelopenia, leukopenia, neutropenia, erythropenia, megakaryopenia, or the like.

Also in this embodiment of the invention, various underlying disease states may be responsible for the hematopoietic deficiency, including various forms of cancer, or other disease states listed in Table I below.

Still another embodiment of the present invention is directed to methods for bone marrow preservation or recovery in a mammal that involve administering one or more therapeutically effective dose(s) of IL-12 to the mammal, without the use of hemtopoietic repopulating cells, hematopoietic progenitor cells or hematopoietic stem cells, for a duration necessary for bone marrow preservation or recovery. These methods are suitable for use to counteract the effects of bone marrow failure or when the mammal is suffering from a disease state and near destruction of the bone marrow is a by-product of a treatment regimen recommended to combat the disease state. These methods of the invention are useful in that the need for a bone marrow transplant may be obviated, thus eliminating the generally negative side effects of such transplants whether they be allogenic or autologous.

These methods include bone marrow preservation or recovery that involves increase in hematopoietic repopulating cell, hematopoietic stem cells or hematopoietic progenitor cells, an increase in one or more differentiated hematopoietic cells types and/or an increase in hematopoietic support cells.

In this embodiment of the invention, as stated above, the deficiency may be a general deficiency in hematopoiesis in the mammal, or the deficiency may include a deficiency in one or more specific hematopoietic cell lineages, such as a low white blood cell count, red blood cell count, platelet count, neutrophil count, monocyte count, lymphocyte count, granulocyte count, dendritic cell count, or the like. These deficient states of hematopoiesis may be characterized as a lymphopenia, myelopenia, leukopenia, neutropenia, erythropenia, megakaryopenia, or the like.

Also in this embodiment of the invention, various underlying disease states may be responsible for the hematopoietic deficiency, including various forms of cancer, or other disease states listed in Table I below.

BRIEF DESCRIPTION OF THE FIGURES

FIG. 2A: 1 day post radiation; FIG. 2B: 12 days post radiation; FIG. 2C: 14 days post radiation. Although there is no significant histological differences at the time points of day 1, 7, and 10 (results were not shown for day 7 and 10), colonies were observed at day 12 in the mice treated with IL-12 (FIG. 2B). At day 14, bone marrow in IL-12 treated mice shows significant regeneration while there is not obvious regeneration in control mice bone marrow. (200× magnification)

FIG. 4A: white blood cell count.

FIG. 6A: white blood cell count; FIG. 6B: red blood cell count; FIG. 6C: platelet count. By day 14 post radiation, all the mice from control group died, but the mice received IL-12 started to recover.

FIG. 9 shows that IL-12 administration promotes multiple lineage blood cell recovery from the hematopoietic insult of chemotherapeutic drugs; IL-12 was administrated at different time (36 hrs before or 12 hrs after cytoxan) to mice who received relatively high doses of the chemotherapeutic drug Cytoxan (300 mg/kg).

DESCRIPTION OF THE INVENTION

Figure 1:
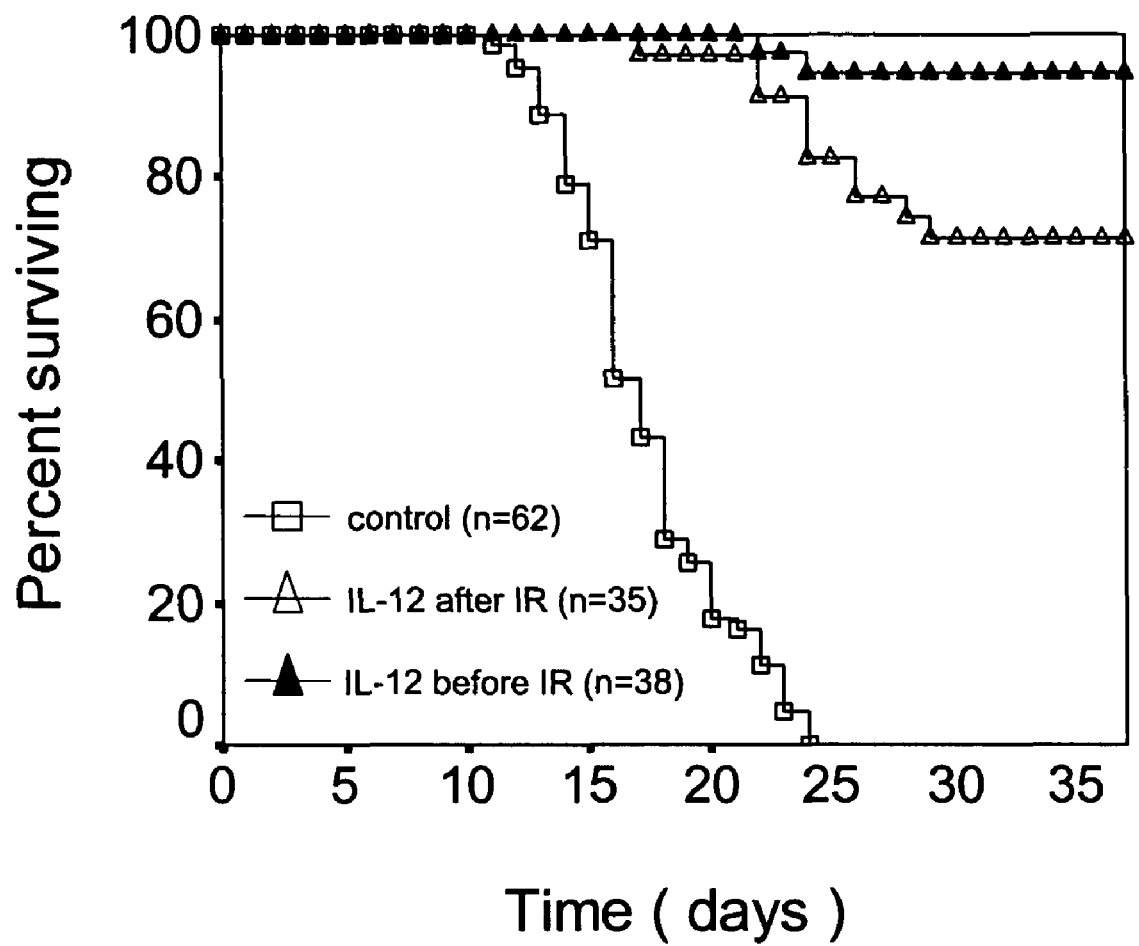
FIG. 1 shows a Kaplan-Meier survival curve for the radioprotective effect of IL-12 administration; the data show that IL-12 protects mice from lethal ionizing radiation.

Embodiments of the present invention provide for various methods of using Interleukin-12 (IL-12) in hematopoiesis, particular for stimulating or enhancing hematopoiesis in a mammal in need. The present invention includes various approaches to using IL-12 to increase the production of hematopoietic cell types or lineages.

A particular embodiment of the present invention is directed to treating a disease state in a mammal, where treatment modalities themselves generally produce decreases or deficiencies in hematopoisis as a limiting toxicity to the treatment modality. Other embodiments of the invention provide for methods of generally treating a mammal for a deficiency in one or more hematopoietic cell types or lineages, methods for stimulating or enhancing hematopoiesis and methods of preservation and recovery cells that comprise bone marrow.

An indication of the therapeutic effectiveness of the therapeutic methods of the present invention is demonstrated by the ability of these methods to confer survival on lethally irradiated animals as illustrated below. Recovery from lethal irradiation provides an extreme indication of the therapeutic effectiveness of the methods of the present invention. However, as shown in the examples below, the therapeutic methods of the present invention can promote hematopoieisis and hematopoietic recovery in the face of less than lethal doses of irradiation, or less than lethal doses of chemotherapeutic agents, or in disease states where increased hematopoiesis is of therapeutic benefit.

The first embodiment of the methods of the invention involves treating the mammal for a generally treatment-induced deficiency in hematopoiesis. The second embodiment of the methods of the invention involves treating the mammal for a deficiency in hematopoiesis where the deficiency is substantially the result of a disease state, but may be exacerbated by treatment modalities. Both embodiments of the invention provide for enhanced hematopoiesis and/or hematopoietic recovery by administering interleukin-12, or a substantial equivalent, to the mammal.

Other embodiments of the present invention provide methods of using IL-12 to promote, stimulate or enhance hematopoiesis and/or hematopoietic recovery in mammals suffering from a deficiency or defect in hematopoiesis. Still other embodiments provide for preservation or recovery of bone marrow by administering IL-12 in accordance with the methods provided herein. Moreover, in all embodiments of the invention, IL-12 promoted, stimulated or enhanced hematopoiesis appears to be largely generated from the level of the hematopoietic repopulating, hematopoietic stem or hematopoietic progenitor cell compartment. Further, the uses of IL-12 in embodiments of the invention are particularly useful as methods of treatment in the medical fields of oncology and hematology.

Definitions:

The following definitions are provided to give clarity to language used within the specification; language used to clarify definitions is meant to be interpreted broadly and generically.

"Disease state" refers to a condition present in a mammal whereby the health and well being of the mammal is compromised. In certain embodiments of the invention, treatments intended to target the disease state are administered to the mammal.

"A treatment" is intended to target the disease state and combat it, i.e., ameliorate the disease state. The particular treatment thus will depend on the disease state to be targeted and the current or future state of medicinal therapies and therapeutic approaches. A treatment may have associated toxicities.

"An associated hematopoietic toxicity" is a toxicity that substantially arises from the administration of the treatment to a mammal that adversely affects the hematopoietic system of the mammal. This adverse effect can be manifested in the mammal broadly whereby many hematopoietic cell types are altered from what is considered to be normal levels, as a result of the treatment, or as a result of the treatment and the disease state combined, or the adverse effect can be manifested in the mammal more specifically whereby only one or a few hematopoietic cell types are altered from what is considered to be normal levels, as a result of the treatment, or as a result of the treatment and the disease state combined.

"Interleukin-12 (IL-12)" refers to any IL-12 molecule that yields at least one of the hematopoietic properties disclosed herein, including native IL-12 molecules, variant 11-12 molecules and covalently modified IL-12 molecules, now known or to be developed in the future, produced in any manner known in the art now or to be developed in the future. Generally, the amino acid sequences of the IL-12 molecule used in embodiments of the invention are derived from the specific mammal to be treated by the methods of the invention. Thus, for the sake of illustration, for humans, generally human IL-12, or recombinant human IL-12, would be administered to a human in the methods of the invention, and similarly, for felines, for example, the feline IL-12, or recombinant feline IL-12, would be administered to a feline in the methods of the invention. Also included in the invention, however, are certain embodiments where the IL-12 molecule does not derive its amino acid sequence from the mammal that is the subject of the therapeutic methods of the invention. For the sake of illustration, human IL-12 or recombinant human IL-12 may be utilized in a feline mammal. Still other embodiments of the invention include IL-12 molecules where the native amino acid sequence of IL-12 is altered from the native sequence, but the IL-12 molecule functions to yield the hematopoietic properties of IL-12 that are disclosed herein. Alterations from the native, species-specific amino acid sequence of IL-12 include changes in the primary sequence of IL-12 and encompass deletions and additions to the primary amino acid sequence to yield variant IL-12 molecules. An example of a highly derivatized IL-12 molecule is the redesigned IL-12 molecule produced by Maxygen, Inc. (Leong S R, et al., Proc Natl Acad Sci USA. 2003 Feb. 4; 100 (3): 1163-8.), where the variant IL-12 molecule is produced by a DNA shuffling method. Also included are modified IL-12 molecules are also included in the methods of invention, such as covalent modifications to the IL-12 molecule that increase its shelf life, half-life, potency, solubility, delivery, etc., additions of polyethylene glycol groups, polypropylene glycol, etc., in the manner set forth in U.S. Pat. Nos. 4,640,835; 4,496,689; 4,301,144; 4,670,417; 4,791,192 or 4,179,337. One type of covalent modification of the IL-12 molecule is introduced into the molecule by reacting targeted amino acid residues of the IL-12 polypeptide with an organic derivatizing agent that is capable of reacting with selected side chains or the N- or C-terminal residues of the IL-12 polypeptide. Both native sequence IL-12 and amino acid sequence variants of IL-12 may be covalently modified. Also as referred to herein, the IL-12 molecule can be produced by various methods known in the art, including recombinant methods. Since it is often difficult to predict in advance the characteristics of a variant IL-12 polypeptide, it will be appreciated that some screening of the recovered variant will be needed to select the optimal variant. A preferred method of assessing a change in the hematological stimulating or enhancing properties of variant IL-12 molecules is via the lethal irradiation rescue protocol disclosed below. Other potential modifications of protein or polypeptide properties such as redox or thermal stability, hydrophobicity, susceptibility to proteolytic degradation, or the tendency to aggregate with carriers or into multimers are assayed by methods well known in the art.

"One or more therapeutically effective dose(s) of IL-12" is any dose administered for any time intervals and for any duration that can substantially ameliorate either the associated hematopoietic toxicity of the treatment intended to target the disease state and/or can substantially ameliorate a hematopoietic deficiency in one or more hematopoietic cell types, or is capable of stimulating hematopoiesis by stimulating or enhancing the proliferation of hematopoietic repopulating cells, hematopoietic progenitor cells or hematopoietic stem cells.

"Near the time of administration of the treatment" refers to the administration of IL-12 at any reasonable time period either before and/or after the administration of the treatment, such as one month, three weeks, two weeks, one week, several days, one day, 20 hours, several hours, one hour or minutes. Near the time of administration of the treatment may also refer to either the simultaneous or near simultaneous administration of the treatment and IL-12, i.e., within minutes to one day.

"Chemotherapy" refers to any therapy that includes natural or synthetic agents now known or to be developed in the medical arts. Examples of chemotherapy include the numerous cancer drugs that are currently available. However, chemotherapy also includes any drug, natural or synthetic, that is intended to treat a disease state. In certain embodiments of the invention, chemotherapy may include the administration of several state of the art drugs intended to treat the disease state. Examples include combined chemotherapy with docetaxel, cisplatin, and 5-fluorouracil for patients with locally advanced squamous cell carcinoma of the head (Tsukuda, M. et al., Int J Clin Oncol. 2004 June; 9 (3): 161-6), and fludarabine and bendamustine in refractory and relapsed indolent lymphoma (Konigsmann M, et al., Leuk Lymphoma. 2004; 45 (9): 1821-1827).

"Radiation therapy" refers to any therapy where any form of radiation is used to treat the disease state. The instruments that produce the radiation for the radiation therapy are either those instruments currently available or to be available in the future.

"High dose treatment modalities" refer to treatments that are high sub-lethal or near lethal. High dose treatment modalities are intended to have an increased ability to combat a disease state, but generally possess increased associated toxicities. Further, generally high dose treatment modalities exhibit increased hematopoietic toxicities, as compared with conventional treatment modalities. The protocols for high dose treatment modalities are those currently used or to be used in the future.

"A dose dense treatment regimen" is generally a treatment regimen whereby the treatment is repeated sequentially in an accelerated manner to achieve the desired treatment outcome, as compared with conventional treatment regimens. The methods of the invention facilitate the use of dose dense treatment regimens by reducing or ameliorating the associated hematopoietic toxicities of the treatment, thereby permitting dose dense treatment regimens to be utilized and increasing the rate of success in treating a particular disease state. (see generally, Hudis C A, Schmits N, Semin Oncol. 2004 June; 31 (3 Suppl 8): 19-26; Keith B et al., J Clin Oncol. 2004 Feb. 15; 22 (4): 749; author reply 751-3; Maurel J et al, Cancer. 2004 Apr. 1; 100 (7): 1498-506; Atkins C D, J Clin Oncol. 2004 Feb. 15; 22 (4): 749-50.)

"Chemoprotection or radioprotection" refers to protection from, or an apparent decrease in, the associated hematopoietic toxicity of a treatment intended to target the disease state.

"An increased remission" refers to a decrease, lessening, reduction, shrinking, diminution, or the like in one or more measurable parameters of a particular disease state.

"Solid tumors" generally refers to the presence of cancer of body tissues other than blood, bone marrow, or the lymphatic system.

"Hematopoietic disorders (cancers)" generally refers to the presence of cancerous cells originated from hematopoietic system.

"Ameliorate the deficiency" refers to a reduction in the hematopoietic deficiency, i.e., an improvement in the deficiency, or a restoration, partially or complete, of the normal state as defined by currently medical practice. Thus, amelioration of the hematopoitic deficiency refers to an increase in, a stimulation, an enhancement or promotion of, hematopoiesis generally or specifically. Amelioration of the hematopoietic deficiency can be observed to be general, i.e., to increase two or more hematopoietic cell types or lineages, or specific, i.e., to increase one hematopoietic cell type or lineages.

"Bone marrow cells" generally refers to cells that reside in and/or home to the bone marrow compartment of a mammal. Included in the term "bone marrow cells" is not only cells of hematopoietic origin, including but not limited to hematopoietic repopulating cells, hematopoietic stem cell and/or progenitor cells, but any cells that may be derived from bone marrow, such as endothelial cells, mesenchymal cells, bone cells, neural cells, supporting cells (stromal cells), including but not limited to the associated stem and/or progenitor cells for these and other cell types and lineages.

"Hematopoietic cell type" generally refers to differentiated hematopoietic cells of various types, but can also include the hematopoietic progenitor cells from which the particular hematopoietic cell types originate from, such as various blast cells refering to all the cell types related to blood cell production, including stem cells, progenitor cells, and various lineage cells, such as myeloid cells, lymphoid cell, etc.

"Hematopoietic cell lineage" generally refers to a particular lineage of differentiated hematopoietic cells, such as myeloid or lymphoid., but could also refer to more differentiated lineages such as dendritic, erythroid, etc.

"IL-12 facilitated proliferation" of cells refers to an increase, a stimulation, or an enhancement of hematopoiesis that at least partially attributed to an expansion, or increase, in cells that generally reside or home to the bone marrow of a mammal, such as hematopoietic progenitor and/or stem cells, but includes other cells that comprise the microenviroment of the bone marrow niche.

"Stimulation or enhancement of hematopoiesis" generally refers to an increase in one or more hematopoietic cell types or lineages, and especially relates to a stimulation or enhancement of one or more hematopoietic cell types or lineages in cases where a mammal has a deficiency in one or more hematopoietic cell types or lineages.

"Hematopoietic long-term repopulating cells" are generally the most primitive blood cells in the bone marrow; they are the blood stem cells that are responsible for providing life-long production of the various blood cell types and lineages.

"Hematopoietic stem cells" are generally the blood stem cells; there are two types: "long-term repopulating" as defined above, and "short-term repopulating" which can produce "progenitor cells" for a short period (weeks, months or even sometimes years depending on the mammal).

"Hematopoietic progenitor cells" are generally the first cells to differentiate from (i.e., mature from) blood stem cells; they then differentiate (mature) into the various blood cell types and lineages.

"Hematopoietic support cells" are the non-blood cells of the bone marrow; these cells provide "support" for blood cell production. These cells are also referred to as bone marrow stromal cells.

"Bone marrow preservation" means the process whereby bone marrow that has been damaged by radiation, chemotherapy, disease or toxins is maintained at its normal, or near normal, state; "bone marrow recovery" means the process whereby bone marrow that has been damaged by radiation, chemotherapy, disease or toxins is restored to its normal, near normal state, or where any measurable improvement in bone marrow function are obtained; bone marrow function is the process whereby appropriate levels of the various blood cell types or lineages are produced from the hematopoietic (blood) stem cells.

"Bone marrow failure" is the pathologic process where bone marrow that has been damaged by radiation, chemotherapy, disease or toxins is not able to be restored to normal and, therefore, fails to produce sufficient blood cells to maintain proper hematopoiesis in the mammal.

Hematopoietic Cell Production:

See generally, U.S. Pat. Nos. 5,968,513, 5,851,984 and 6,159,462. The morphologically recognizable and functionally capable cells circulating in blood include erythrocytes, macrophage or monocyte, neutrophilic, eosinophilic, and basophilic granulocytes, B-, T, non B-, non T-lymphocytes, and platelets. These mature hematopoietic cells derive from and are replaced, on demand, by morphologically recognizable dividing precursor cells for the respective lineages such as erythroblasts for the erythrocyte series, myeloblasts, promyelocytes and myelocytes for the monotyte/macrophage and granulocyte series, and megakaryocytes for the platelets.

The precursor cells derive from more primitive cells that can simplistically be divided into two major subgroups: stem cells and progenitor cells. The definitions of stem and progenitor cells are operational and depend on functional, rather than on morphological, criteria. Stem cells have extensive self-renewal or self-maintenance capacity, a necessity since an absence or depletion of these cells could result in the complete depletion of one or more cell lineages or cell types, events that would lead within a short time to disease and death. Some of the stem cells differentiate upon need, but some stem cells or their daughter cells produce other stem cells to maintain the precious pool of these cells. Thus, in addition to maintaining their own kind, pluripotential stem cells, or hemtopoietic repopulating cells, are capable of differentiation into several sub-lines of progenitor cells with more limited self-renewal capacity or no self-renewal capacity. These progenitor cells ultimately give rise to the morphologically recognizable precursor cells. The progenitor cells are capable of proliferating and differentiating along one, or more than one, of the myeloid differentiation pathways (Lajtha, L. G. (Rapporteur), 1979, Blood Cells 5:447).

Additionally, chemotherapy and radiation therapy used in the treatment of cancer and certain immunological disorders can cause pancytopenias or combinations of anemia, neutropenia and thrombocytopenia. Thus, the increase or replacement of hematopoietic cells is often crucial to the success of such treatments. (For a general discussion of hematological disorders and their causes, see, e.g., "Hematology" in Scientific American Medicine, E. Rubenstein and D. Federman, eds., Volume 2, chapter 5, Scientific American, New York (1996)).

Furthermore, aplastic anemia presents a serious clinical condition as the overall mortality of all patients with aplastic anemias, in the absence of stem cell therapy, is high. Approximately 60-75% of individuals suffering from the disorder die within 12 months, in the absence of new stem cells. The overall incidence of these diseases is approximately 25 new cases per million persons per year. Although it is extremely unlikely that a single pathogenic mechanism accounts for all aplastic anemias, it is clear that provision of new hematopoietic stem cells is usually sufficient to allow permanent recovery, since transplantation of patients with aplastic anemia with bone marrow obtained from identical twins (i.e., syngeneic) (Pillow, R. P., et al., 1966, N. Engl. J. Med. 275:94-97) or from HLA-identical siblings (i.e., allogeneic) (Thomas, E. D., et al., Feb. 5, 1972, The Lancet, pp. 284-289) can fully correct the disease. However, some patients with aplastic anemia reject the transplanted marrow. This complication is particularly common among patients who have been immunologically sensitized as a result of multiple therapeutic blood transfusions.

The current therapy available for many hematological disorders as well as the destruction of the endogenous hematopoietic cells caused by chemotherapy or radiotherapy is bone marrow transplantation. However, use of bone marrow transplantation is severely restricted since it is extremely rare to have perfectly matched (genetically identical) donors, except in cases where an identical twin is available or where bone marrow cells of a patient in remission are stored in a viable frozen state. Except in such autologous cases, there is an inevitable genetic mismatch of some degree, which entails serious and sometimes lethal complications. These complications are two-fold. First, the patient is usually immunologically incapacitated by drugs beforehand, in order to avoid immune rejection of the foreign bone marrow cells (host versus graft reaction). Second, when and if the donated bone marrow cells become established, they can attack the patient (graft versus host disease), who is recognized as foreign. Even with closely matched family donors, these complications of partial mismatching are the cause of substantial mortality and morbidity directly due to bone marrow transplantation from a genetically different individual.

Peripheral blood has also been investigated as a source of repopulating cells, or stem cells for hematopoietic reconstitution (Nothdurtt, W., et al., 1977, Scand. J. Haematol. 19:470-481; Sarpel, S. C., et al., 1979, Exp. Hematol. 7:113-120; Ragharachar, A., et al., 1983, J. Cell. Biochem. Suppl. 7A:78; Juttner, C. A., et al., 1985, Brit. J. Haematol. 61:739-745; Abrams, R. A., et al., 1983, J. Cell. Biochem. Suppl. 7A: 53; Prummer, O., et al., 1985, Exp. Hematol. 13:891-898). In some studies, promising results have been obtained for patients with various leukemias (Reiffers, J., et al., 1986, Exp. Hematol. 14:312-315; Goldman, J. M., et al., 1980, Br. J. Haematol. 45:223-231; Tilly, H., et al., Jul. 19, 1986, The Lancet, pp. 154-155; see also To, L. B. and Juttner, C. A., 1987, Brit. J. Haematol. 66: 285-288, and references cited therein); and with lymphoma (Korbling, M., et al., 1986, Blood 67:529-532). Other studies using peripheral blood, however, have failed to effect reconstitution (Hershko, C., et al., 1979, The Lancet 1:945-947; Ochs, H. D., et al., 1981, Pediatr. Res. 15:601). Studies have also investigated the use of fetal liver cell transplantation (Cain, G. R., et al., 1986, Transplantation 41:32-25; Ochs, H. D., et al., 1981, Pediatr. Res. 15:601; Paige, C. J., et al., 1981, J. Exp. Med. 153:154-165; Touraine, J. L., 1980, Excerpta Med. 514:277; Touraine, J. L., 1983, Birth Defects 19:139; see also Good, R. A., et al., 1983, Cellular Immunol. 82:44-45 and references cited therein) or neonatal spleen cell transplantation (Yunis, E. J., et al., 1974, Proc. Natl. Acad. Sci. U.S.A. 72:4100) as stem cell sources for hematopoietic reconstitution. Cells of neonatal thymus have also been transplanted in immune reconstitution experiments (Vickery, A. C., et al., 1983, J. Parasitol. 69 (3): 478-485; Hirokawa, K., et al., 1982, Clin. Immunol. Immunopathol. 22:297-304).

Interleukin-12 (IL-12):

For general descriptions relating IL-12, see U.S. Pat. Nos. 5,573,764, 5,648,072, 5,648,467, 5,744,132, 5,756,085, 5,853,714 and 6,683,046. Interleukin-12 (IL-12) is a heterodimeric cytokine generally described as a proinflamatory cytokine that regulates the activity of cells involved in the immune response (Fitz K M, et al., 1989, J. Exp. Med. 170: 827-45). Generally IL-12 stimulates the production of interferon-γ (INF-γ) from natural killer (NK) cells and T cells (Lertmemongkolchai G, Cai et al., 2001, Journal of Immunology. 166:1097-105; Cui J, Shin T, et al., 1997, Science. 278:1623-6; Ohteki T, Fukao T, et alk., 1999, J. Exp. Med. 189:1981-6; Airoldi I, Gri G, et al., 2000, Journal of Immunology. 165:6880-8), favors the differentiation of T helper 1 (TH1) cells (Hsieh C S, et al., 1993, Science. 260:547-9; Manetti R, et al., 1993, J. Exp. Med. 177:1199-1204), and forms a link between innate resistance and adaptive immunity. IL-12 has also been shown to inhibit cancer growth via its immuno-modulatory and anti-angiogenesis effects (Brunda M J, et al., 1993, J. Exp. Med. 178:1223-1230; Noguchi Y, et al., 1996, Proc. Natl. Acad. Sci. U.S.A. 93:11798-11801; Giordano P N, et al., 2001, J. Exp. Med. 194:1195-1206; Colombo M P, et al, 2002, Cytokine Growth factor rev. 13:155-168; Yao L, et al., 2000, Blood 96:1900-1905). IL-12 is produced mainly by dendritic cells (DC) and phagocytes (macrophages and neutrophils) once they are activated by encountering pathogenic bacteria, fingi or intracellular parasites (Reis C, et al., 1997, J. Exp. Med. 186:1819-1829; Gazzinelli R T, et al., 1994, J. Immunol. 153:2533-2543; Dalod M, et al., 2002, J. Exp. Med. 195:517-528). The IL-12 receptor (IL-12 R) is expressed mainly by activated T cells and NK cells (Presky D H, et al., 1996, Proc. Natl. Acad. Sci. U.S.A. 93:14002-14007; Wu C Y, et al., 1996, Eur J. Immunol. 26:345-50).

Generally the production of IL-12 stimulates the production of INF-γ, which, in turn, enhances the production of IL-12, thus forming a positive feedback loop. In in vitro systems, it has been reported that IL-12 can synergize with other cytokines (IL-3 and SCF for example) to stimulate the proliferation and differentiation of early hematopoietic progenitors (Jacobsen S E, et al., 1993, J. Exp Med 2: 413-8; Ploemacher R E, et al., 1993, Leukemia 7: 1381-8; Hirao A, et al., 1995, Stem Cells 13: 47-53).

However, prior to the present invention, in vivo administration of IL-12 was observed to decrease peripheral blood cell counts and bone marrow hematopoiesis (Robertson M J, et al., 1999, Clinical Cancer Research 5: 9-16; Lenzi R, et al., 2002, Clinical Cancer Research 8:3686-95; Ryffel B. 1997, Clin Immunol Immunopathol. 83:18-20; Car B D, et al., 1999, The Toxicol Pathol. 27:58-63). Using INF-γ receptor knockout mice, Eng et al and Car et al demonstrated that high dose IL-12 did not induce the commonly seen toxicity effect, i.e., there was no inhibition of hematopoiesis (Eng V M, et al., 1995, J. Exp Med. 181:1893-8; Car B D, et al., 1995, American Journal of Pathology 147:1693-707). This observation suggests that the general phenomenon of IL-12 facilitated enhancement of differentiated hematopoietic cells, as reported previously, may be balanced in vivo by the production of INF-γ, which acts in a dominant myelo-suppressive fashion.

Without being held to any particular theory, the inventors hypothesize that, in contrast to previous reports regarding the mechanistic pathway for IL-12 mediated proliferation of hematopoietic cells, when the hematopoietic system is compromised, as it is during chemotherapy or radiation therapy, or in the case of certain hematopoietic diseases and disorders that lead to one or more hematopoietic deficiencies, the Il-12 mediated pathway leading to the production of INF-γ may be altered. Thus, besides the low doses used in the examples disclosed herein, another possible mechanism for decreased hematopoietic side effects in embodiments of the invention is that when relatively low dose IL-12 is given to a mammal whose hematopoietic system is compromised, the IL-12/INF-γ positive feedback loop may be inhibited. Since INF-γ inhibits hematopoiesis and also appears to be the major cytokine responsible for toxicity, the interruption of INF-γ production may be one of the factors underlying the discovery by the inventors that administration of IL-12 provides a hematopoietic protective and recovery effect without apparent toxicity.

Therapeutic Methods of the Invention:

The present invention relates to therapeutic methods for treating diseases and disorders in which increased amounts of hematopoietic cells are desirable (e.g., diseases or disorders associated with reduced numbers of one or more hematopoietic cell types or lineages, or diseases where the recommended therapy has associated hematopoietic toxicities, thus leading to reduced numbers of one or more hematopoietic cell types or lineages, such as cancer) by administration of IL-12, derivatives and analogs thereof. Thus, embodiments of the invention provide for methods of alleviating or treating various hematopoietic cell deficiencies, including deficiencies in hematopoietic repopulating cells, progenitor and stem cells, as well as general bone marrow deficiencies, by the direct administration of IL-12 to a mammal, as disclosed herein.

In the first embodiment of the invention, methods are disclosed for treating a disease state in a mammal by administering a treatment to the mammal that is intended to target the disease state, where the treatment has an associated hematopoietic toxicity, in conjunction with the administration of one or more therapeutically effective dose(s) of IL-12 near the time of administration of the treatment. One effect of the administration of IL-12 to the mammal in this embodiment of the invention is reduction of the hematopoietic toxicity of the treatment, thus permitting high-dose and dose dense protocols to be utilized in designed a particular patient's therapeutic regimen.

In a second embodiment of the invention, methods are disclosed for administration of IL-12 directly to a mammal, preferably a human, suffering from a disease or disorder amenable to treatment by increasing production of one or more hematopoietic cell types (e.g., a disease or disorder associated with a hematopoietic cell deficiency). In a third embodiment of the invention, methods of stimulating hematopoiesis in a mammal in need comprising administering one or more therapeutically effective dose(s) of IL-12 for a duration to achieve a therapeutic effect that includes the stimulation of hematopoiesis, wherein the stimulation of hematoapoiesis involves the IL-12 facilitated proliferation of hematopoietic repopulating cells, hematopoietic progenitor cells or hematopoietic stem cells. In a fourth embodiment of the invention, methods are disclosed for bone marrow preservation or recovery in a mammal by administering one or more therapeutically effective dose(s) of IL-12 to the mammal, without the use of bone marrow cells, hematopoietic progenitor cells or hematopoietic stem cells, for a duration necessary for bone marrow preservation or recovery.

A further aspect of certain embodiments of the invention is that the use of IL-12 as an adjuvant or ancillary therapy to alleviate the hematopoietic toxicities associated with various forms of radiation and chemotherapy, permits high-dose and dose dense treatment protocols to be utilized, and thus, achieve greater rates of remission of the particular disease state and overall patient survival.

A particular embodiment of the invention provide for methods of treating a disease state in a mammal. In this embodiment, the disease state can be any disease state that is treated with either any chemotherapy or radiation therapy, or both. In the invention, the combined use of chemotherapeutic agents is preferred, as this clinical protocol is generally thought to be more therapeutically effective.

These methods generally include administering a treatment to the mammal that is intended to target the disease state. In this embodiment, the treatment, which is intended to combat the disease state, also has an associated hematopoietic toxicity. A second component in this embodiment of the invention includes administering a therapeutically effective dose of IL-12 near the time of administration of the treatment. IL-12 can be administered at any point in time near the administration of the treatment that yields the desired therapeutic effect. An overall benefit of practicing this embodiment of the invention is that the administration of IL-12 to the mammal reduces or decreases the hematopoietic toxicity of the treatment, and as a consequence alters the limiting toxic dosage of the various treatment modalities.

In these embodiments, the methods generally involve administering a primary therapeutic to a mammal, along with a secondary therapeutic in the form of IL-112, where the secondary therapeutic, i.e., IL-12 enhances hematopoiesis or improves hematopoietic recovery as compared with the administration of the primary therapeutic alone. The preferred mammal in this embodiment of the invention is a human.

The treatment that is intended to target the disease state can be any currently practiced therapy, or any therapy to be developed that uses either chemotherapy or radiation therapy, or a combined therapy, to attempt to combat the disease state. In the invention, chemotherapy involves the administration of chemical agents, which can be natural or synthetic agent that are provided in any chemical state, e.g. monomer to highly polymeric species. In the invention, radiation therapy includes the administration of relatively high energy wavelengths of light or high energy particles to the mammal as the treatment modality. For either chemotherapy or radiation therapy, high dose therapeutic approaches and dose dense protocols as currently practiced or to be developed in the future can be used in the embodiments of the present invention.

In general, disorders that can be treated by methods of the invention include, but are not limited to, four broad categories. First are diseases resulting from a failure or dysfunction of normal blood cell production and maturation (i.e., aplastic anemia, cytopenias and hypoproliferative stem cell disorders). The second group are neoplastic, malignant diseases in the hematopoietic organs (e.g., leukemia and lymphomas). The third group of disorders comprises those of patients with a broad spectrum of malignant solid tumors of non-hematopoietic origin. Induction of hematopoietic cell proliferation in these patients serves as a bone marrow rescue procedure, without the use of a cellular transplant, which is provided to a patient as an adjuvant therapy to chemotherapy and/or radiation therapy, including otherwise lethal chemotherapy or radiation therapy and dose dense therapeutic protocols. The fourth group of diseases consists of autoimmune conditions, where the enhancement or stimulation of hematopoiesis, leading to increases in hematopoietic cells, can serve as a source of replacement of an abnormal immune system. Particular diseases and disorders which can be treated by induction of hematopoietic cell production in vivo are not limited to those listed in Table 1, and described infra.

TABLE I

DISEASES STATES OR DISORDERS WHICH CAN
BE TREATED BY INCREASING HEMATOPOIESIS

I. Diseases resulting from a failure or dysfunction of
normal blood cell production and maturation hypoproliferative stem cell disorders
hyperproliefeative stem cell disorders
aplastic anemia
neutropenia
cytopenia
anemia
pancytopenia
agranulocytosis

TABLE I-continued

DISEASES STATES OR DISORDERS WHICH CAN BE TREATED BY INCREASING HEMATOPOIESIS thrombocytopenia
red cell aplasia
Blackfan-Diamond syndrome
due to drugs, radiation, or infection
II. Hematopoietic malignancies acute lymphoblastic (lymphocytic) leukemia
chronic lymphocytic leukemia
acute myelogenous leukemia
chronic myelogenous leukemia
acute malignant myelosclerosis
multiple myeloma
polycythemia vera
agnogenic myelometaplasia
Waldenstrom's macroglobulinemia
Hodgkin's lymphoma
non-Hodgkin's lymphoma
III. Immunosuppression in subjects with malignant, solid tumors malignant melanoma
non-small cell lung cancer
carcinoma of the stomach
ovarian carcinoma
breast carcinoma
small cell lung carcinoma
retinoblastoma
testicular carcinoma
glioblastoma
rhabdomyosarcoma
neuroblastoma
Ewing's sarcoma
Lymphoma
IV. Autoimmune diseases rheumatoid arthritis
diabetes type I
chronic hepatitis
multiple sclerosis
systemic lupus erythematosus
V. Genetic (congenital) disorders anemias
familial aplastic anemias
Fanconi's syndrome
Bloom's syndrome
pure red cell aplasia (PRCA)
dyskeratosis congenita
Blackfan-Diamond syndrome
congenital dyserythropoietic syndromes I–IV
Shwachmann-Diamond syndrome
dihydrofolate reductase deficiencies
formamino transferase deficiency
Lesch-Nyhan syndrome
congenital spherocytosis
congenital elliptocytosis
congenital stomatocytosis
congenital Rh null disease
paroxysmal nocturnal hemoglobinuria
G6PD (glucose-6-phosphate dehydrogenase) variants 1, 2, 3
pyruvate kinase deficiency
congenital erythropoietin sensitivity deficiency
sickle cell disease and trait
thalassemia alpha, beta, gamma
met-hemoglobinemia
congenital disorders of immunity
severe combined immunodeficiency disease (SCID)
barelymphocyte syndrome
ionophore-responsive combined immunodeficiency
combined immunodeficiency with a capping abnormality
nucleoside phosphorylase deficiency
granulocyte actin deficiency
infantile agranulocytosis
Gaucher's disease
adenosine deaminase deficiency
Kostmann's syndrome
reticular dysgenesis
congenital leukocyte dysfunction syndromes

TABLE I-continued

DISEASES STATES OR DISORDERS WHICH CAN BE TREATED BY INCREASING HEMATOPOIESIS

VI. Others osteopetrosis
myelosclerosis
acquired hemolytic anemias
acquired immunodeficiencies
infectious disorders causing primary or secondary immunodeficiency
bacterial infections (e.g. Brucellosis, Listeriosis, tuberculosis, leprosy)
parasitic infections (e.g. malaria, Leishmaniasis)
fungal infections
disorders involving disproportions in lymphoid cell sets and impaired immune functions due to aging
phagocyte disorders
Kostmann's agranulocytosis
chronic granulomatous disease
Chediak-Higachi syndrome
Willams-Beuren syndrome
neutrophil actin deficiency
neutrophil membrane GP-180 deficiency
metabolic storage diseases
mucopolysaccharidoses
mucolipidoses
miscellaneous disorders involving immune mechanisms
Wiskott-Aldrich Syndrome
alpha 1-antitrypsin deficiency a) Diseases Resulting from a Failure or Dysfunction of Normal Blood Cell Production and Maturation In a preferred embodiment of the invention, 1'-12 administration in accordance with the methods of the invention is used to treat a disease resulting from a failure or dysfunction of normal blood cell production and maturation, such as an aplastic anemia, a cytopenia or a hypoproliferative stem cell disorder. These disorders entail failure of stem cells in bone marrow to provide normal numbers of functional blood cells. The aplastic anemias result from the failure of stem cells to give rise to the intermediate and mature forms of red cells, white cells, and platelets. While red cell production is usually most seriously affected, a marked decrease in production of other mature blood cell elements is also seen as some anemias specifically affect production of white cells and/or platelets. The large majority of these anemias are acquired during adult life, and do not have any apparent genetic predisposition. About half of these acquired anemias arise in the absence of any obvious causative factor such as exposure to poisons, drugs or disease processes that impair stem cell function; these are termed idiopathic aplastic anemias. The remaining cases are associated with exposure to an extremely diverse array of chemicals and drugs and also occur as the consequence of viral infections and after pregnancy. Other specific types of aplastic anemia are termed agranulocytosis or thrombocytopenia to indicate that the major deficiency lies in particular white cells or in platelet production, respectively. Additionally, agranulocytosis may be associated with autoimmune syndromes such as systemic lupus erythematosus (SLE) or with other infections, such as neonatal rubella.

In addition, immune deficiencies which are the primary or secondary result of infection by pathogenic microorganisms can be treated by administration of 11-12 according to the methods disclosed in the present invention. Microorganisms causing immune deficiencies which may be treated according to this embodiment of the invention include but are not limited to gram-negative bacilli such as Brucella or Listeria, the mycobacterium which are the etiological agents of tuberculosis or of Hansen's disease (leprosy), parasites such as Plasmodium (the etiological agents of malaria) or Leishmania, and fuigi (such as those that cause pneumonia and other lethal infections secondary to immunodeficiencies) (for a discussion of many of these disorders, see Harrison's Principles of Internal Medicine, 1970, 6th Edition, Wintrobe, M. M., et al., eds., McGraw-Hill, New York, pp. 798-1044).

b) Treatment of Malignancies

Both chemotherapy and radiation therapy, which are used, either singly or together, to combat various forms of cancer, and other disease states, are toxic to an individual's hematopoietic system. Thus, for individuals treated with chemotherapy, radiation therapy, or a combination of these two therapeutic modalities, the individual's blood supply can be substantially depleted. Moreover, this depletion of the blood supply is generally a limiting factor in the use of chemotherapy and/or radiation therapy to combat various cancers and other disease states, and therefore generally precludes the use of high dose or dose dense treatment regimens.

Previously, IL-12 has been reported to play a pivotal role as an immuno-modulator, and has previously been shown to inhibit tumor growth in mice, IL-12 h as been tested in phase I and II human clinical trials for its potential to stimulate an immune response in cancer therapy (Eng V M et al., Journal of Experimental Medicine 181:1893-8; Car B D et al., American Journal of Pathology 147: 1693-707). One of the common side effects of IL-12 therapy, however, is a transient decrease in blood cell counts: lymphopenia is common (Eng V M et al., Journal of Experimental Medicine 181:1893-8; Car B D et al., American Journal of Pathology 147: 1693-707). In animal toxicity studies, lymphopenia is also a common side effect (Neta R, et al., J. Immunol. 153:4230-7; Hayes M P et al., Blood 91:4645-4651).

In contrast to previous studies, however, the inventors have made the discovery that when IL-12 is administered during certain time "windows" in relation to the time of a primary therapy, such as chemotherapy or radiation therapy, administration of IL-12 increases the nadir of blood cell counts broadly, i.e., increases blood cell counts, without any observable toxic effects of the IL-12 administration.

Thus, the therapeutic methods of the present invention can promote hematopoiesis in general, and in particular, promote hematopoiesis in an individual who has undergone, is undergoing, or will undergo chemotherapy and/or radiation therapy as treatment regimens that target the particular malignancies. Thus, in the particular embodiments of the invention, IL-12 administration is used as an adjuvant or ancillary therapy to one or more primary therapies implemented near the time of administration of the primary therapy. Thus, the present invention enhances hematopoietic recovery, as well as the general recovery, of a subject undergoing one or more therapies that incidentally decreases the individual's blood supply. As used herein, the term "undergoing" encompasses the implementation of a primary therapy before, during and/or after the implementation of the ancillary therapy of the present invention.

Among the individual-derived benefits that are a consequence of using the methods of the present invention as an adjuvant or ancillary therapy to chemotherapy and/or radiation therapy is a decrease in the toxic side effects of these primary therapeutic modalities, as well as enhanced recovery from these toxic side effects. These toxic side effects include depletion of one or more blood components of the subject's hematopoietic system. A particular individual-derived benefit of administering the methods of the present invention is that more aggressive primary treatment modalities can be used to combat the targeted disease state. Thus, the use of the methods of the present invention as an adjuvant or ancillary therapy allows the primary therapy to be administered in a dose dense treatment modality or high dose modality. In turn, the likelihood of success of the primary therapy is substantially increased when therapeutic compositions including IL-12 are administered as an ancillary therapy or combination therapy along with traditional therapeutic modalities. Another use of the therapeutic methods of the present invention is in the treatment of bone marrow failure resulting from certain disease states or is induced by the use of certain treatment modalities, such as aggressive chemotherapy and/or radiation therapy.

Hyperproliferative malignant stem cell disorders as well as non-hematopoietic malignancies can be treated with chemotherapy and/or radiation therapy along with rescue of hematopoietic cells by direct administration IL-12 as disclosed herein. The conditions that can be treated according to the invention include, but are not limited to, the leukemias listed in Table 1 and the solid tumors listed in Table 1.

These malignancies are currently treated by, inter alia, chemotherapy and/or radiation therapy, when feasible, allogeneic bone marrow transplantation. However, allogeneic HLA identical sibling bone marrow is available only to less than one-third of patients, and this treatment is associated with transplantation-related complications such as immunodeficiency and graft versus host disease. Induction of hematopoietic cell proliferation in vivo via the methods of the invention permits hematopoietic reconstitution of patients lacking suitable allogeneic donors, or in the case of an autologous transplant, eliminates the risk of reintroduction of malignant cells. Thus, the methods of the invention can be administered to a patient who has undergone chemotherapy and/or radiation therapy for treatment of cancer or an immunological disorder. Also included in this embodiment of the invention is the use of administration of IL-12 as an adjuvant therapy to the various therapies used to treat infection, such as HAART therapy and/or radiation therapy, such as total lymphoid irradiation described below.

c) Autoimmune Disorders

Many chronic inflammatory and degenerative diseases are characterized by a continuous immune reaction against the body's own tissues. Such autoimmune disorders include but are not limited to rheumatoid arthritis and other inflammatory osteopathies, diabetes type I, chronic hepatitis, multiple sclerosis, and systemic lupus erythematosus. Autoimmune disorders are often treated by lymphoid irradiation. Administration of 11-12 as disclosed herein can be valuable to repopulate the hematopoietic system after radiotherapy.

Anti-inflammatory drugs such as steroids retard the inflammatory cells which are activated by autoreactive T cells, but do not prevent T cells which recognize self-proteins from activating new inflammatory cells. A more direct approach to treating autoimmune diseases depends on eradication of T cells by irradiation of the lymphoid tissues, and relying on stem cells from the unirradiated bone marrow to repopulate the patient's hematopoietic system. The rationale is that the formation of new populations of mature T cells from bone marrow stem cells may result in absence of T cells that have reactivity to self-specific antigens. This procedure, called total lymphoid irradiation (TLI), has been used to treat intractable rheumatoid arthritis (Strober, S., et al., 1985, Annals of Internal Medicine 102:441-449, 450-458). These clinical trials showed that in the majority of otherwise intractable cases, joint disease was significantly alleviated for at least 2-3 years. However, the major drawback to such treatment is failure of stem cells in the bone marrow of these elderly patients to efficiently repopulate the hematopoietic system, resulting in infections and bleeding disorders. Analogous studies have been made of the effects of TLI as an alternative to cytotoxic drugs for treatment of SLE (Strober, S., et al., 1985, Ann. Internal Med. 102:450). Studies of the use of TLI to treat intractable SLE have also shown that this treatment alleviates disease activity, but is severely limited by failure of bone marrow stem cells to rapidly and efficiently repopulate the hematopoietic system after irradiation. Thus, the therapeutic methods of the invention can be administered to promote proliferation of the remaining hematopoietic cells to increase the success of TLI therapy.

d) Methods of Administration of IL-12

The invention provides methods of treatment by administration to a subject of one or more effective dose(s) of IL-12 for a duration to achieve the desired therapeutic effect. The subject is preferably a mammal, including, but not limited to, animals such as cows, pigs, horses, chickens, cats, dogs, etc., and is most preferably human.

Various delivery systems are known and can be used to administer IL-12 in accordance with the methods of the invention, e.g., encapsulation in liposomes, microparticles, microcapsules, recombinant cells capable of expressing IL-12, receptor-mediated endocytosis (see, e.g., Wu and Wu, 1987, J. Biol. Chem. 262:4429-4432), construction of nucleic acid comprising a gene for IL-12 as part of a retroviral or other vector, etc. Methods of introduction include but are not limited to intradermal, intramuscular, intraperitoneal, intravenous, subcutaneous, intranasal, epidural, and oral routes.

In accordance with the methods of the invention, IL-12 can be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce pharmaceutical compositions comprising IL-12 into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. It may be desirable to administer the pharmaceutical compositions comprising IL-12 locally to the area in need of treatment; this may be achieved, for example and not by way of limitation, by topical application, by injection, by means of a catheter, by means of a suppository, or by means of an implant, said implant being of a porous, non-porous, or gelatinous material, including membranes, such as sialastic membranes, or fibers.

Other modes of IL-12 administration involve delivery in a vesicle, in particular a liposome (see Langer, Science 249: 1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

Still other modes of administration of IL-12 involve delivery in a controlled release system. In certain embodiments, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). Additionally polymeric materials can be used (see Medical Applications of Controlled Release, Langer and Wise (eds.), CRC Pres, Boca Raton, Fla. (1974); Controlled Drug Bioavailability, Drug Product Design and Performance, Smolen and Ball (eds.), Wiley, N.Y. (1984); Ranger and Peppas, J. Macromol. Sci. Rev. Macromol. Chem. 23:61 (1983; see also Levy et al., Science 228:190 (1985); During et al., Ann. Neurol. 25:351 (1989); Howard et al., J. Neurosurg. 71:105 (1989)), or a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

e) Forms and Dosages of IL-12

Suitable dosage forms of IL-12 for use in embodiments of the present invention encompass physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms of IL-12 polypeptides include polysaccharides such as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations.

Suitable examples of sustained-release preparations include semipermeable matrices of solid hydrophobic polymers containing the polypeptide, which matrices are in the form of shaped articles, e.g. films, or microcapsules. Examples of sustained-release matrices include polyesters, hydrogels (for example, poly(2-hydroxyethyl-methacrylate) as described by Langer et al., supra and Langer, supra, or poly(vinylalcohol), polylactides (U.S. Pat. No. 3,773,919), copolymers of L-glutamic acid and .gamma. ethyl-L-glutamate (Sidman et al, supra), non-degradable ethylene-vinyl acetate (Langer et al., supra), degradable lactic acid-glycolic acid copolymers such as the Lupron Depot™ (injectable microspheres composed of lactic acid-glycolicacid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated IL-12 polypeptides remain in the body for a long time, they may denature or aggregate as a result of exposure to moisture at 37.degree. C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release IL-12 containing compositions also include liposomally entrapped polypeptides. Liposomes containing a IL-12 polypeptide are prepared by methods known in the art, such as described in Eppstein et al., Proc. Natl. Acad. Sci. USA 82:3688-3692 (1985); Hwang et al., Proc. Natl. Acad. Sci. USA 77:4030 (1980); and U.S. Pat. Nos. 4,485,045 and 4,544,545. Ordinarily, the liposomes are the small (about 200-800 Angstroms) unilamelar type in which the lipid content is greater than about 30 mol. % cholesterol, the selected proportion being adjusted for the optimal Wnt polypeptide therapy. Liposomes with enhanced circulation time are disclosed in U.S. Pat. No. 5,013,556.

For the treatment of disease, the appropriate dosage of a IL-12 polypeptide will depend on the type of disease to be treated, as defined above, the severity and course of the disease, previous therapy, the patient's clinical history and response to the IL-12 therapeutic methods disclosed herein, and the discretion of the attending physician. In accordance with the invention, IL-12 is suitably administered to the patient at one time or over a series of treatments.

Depending on the type and severity of the disease, about 10 ng/kg to 2000 ng/kg of IL-12 is an initial candidate dosage for administration to the patient, whether, for example, by one or more separate administrations, or by continuous infusion. Humans can safely tolerate a repeated dosages of about 500 ng/kg, but single dosages of up to about 200 ng/kg should not produce toxic side effects. For example, the dose may be the same as that for other cytokines such as G-CSF, GM-CSF and EPO. For repeated administrations over several days or longer, depending on the condition, the treatment is sustained until a desired suppression of disease symptoms occurs. However, other dosage regimens may be useful. The progress of this therapy is easily monitored by conventional techniques and assays.

Il-12 may be administered along with other cytokines, either by direct co-administration or sequential administration. When one or more cytokines are co-administered with IL-12, lesser doses of IL-12 may be employed. Suitable doses of other cytokines, i.e. other than IL-12, are from about 1 ug/kg to about 15 mg/kg of cytokine. For example, the dose may be the same as that for other cytokines such as G-CSF, GM-CSF and EPO. The other cytokine(s) may be administered prior to, simultaneously with, or following administration of IL-12. The cytokine(s) and IL-12 may be combined to form a pharmaceutically composition for simultaneous administration to the mammal. In certain embodiments, the amounts of IL-12 and cytokine are such that a synergistic repopulation of blood cells (or synergistic increase in proliferation and/or differentiation of hematopoietic cells) occurs in the mammal upon administration of IL-12 and other cytokine thereto. In other words, the coordinated action of the two or more agents (i.e. the Il-12 and one or more cytokine(s)) with respect to repopulation of blood cells (or proliferation/differentiation of hematopoietic cells) is greater than the sum of the individual effects of these molecules.

Therapeutic formulations of IL-12 are prepared for storage by mixing IL-12 having the desired degree of purity with optional physiologically acceptable carriers, excipients, or stabilizers (Remington's Pharmaceutical Sciences, 16th edition, Osol, A., Ed., (1980)), in the form of lyophilized cake or aqueous solutions. Acceptable carriers, excipients, or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or non-ionic surfactants such as Tween®, Pluronics™ or polyethylene glycol (PEG).

IL-12 also may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles, and nanocapsules), or in macroemulsions. Such techniques are disclosed in Remington's Pharmaceutical Sciences, supra.

Il-12 to be used for in vivo administration must be sterile. This is readily accomplished by filtration through sterile filtration membranes, prior to or following lyophilization and reconstitution. Il-12 ordinarily will be stored in lyophilized form or in solution. Therapeutic IL-12 compositions generally are placed into a container having a sterile access port, for example, an intravenous solution bag or vial having a stopper pierceable by a hypodermic injection needle.

When applied topically, 11-12 is suitably combined with other ingredients, such as carriers and/or adjuvants. There are no limitations on the nature of such other ingredients, except that they must be physiologically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, IL-12 formulated in a liquid composition may be mixed with an effective amount of a water-soluble polysaccharide or synthetic polymer such as PEG to form a gel of the properviscosityto be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the IL-12 molecule held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight PEGs to obtain the proper viscosity. For example, a mixture of a PEG of molecular weight 400-600 with one of molecularweight 1500 would be effective for this purpose when mixed in the proper ratio to obtain a paste.

The term "water soluble" as applied to the polysaccharides and PEGs is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2-5%, more preferably about 3%, of the gel and Il-12 is present in an amount of about 300-1000 mg per ml of gel.

An effective amount of IL-12 to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer IL-12 until a dosage is reached that achieves the desired effect. A typical daily dosage for systemic treatment might range from about 10 ng/kg to up to 2000 ng/kg or more, depending on the factors mentioned above. As an alternative general proposition, the IL-12 receptor is formulated and delivered to the target site or tissue at a dosage capable of establishing in the tissue an IL-12 level greater than about 0.1 ng/cc up to a maximum dose that is efficacious but not unduly toxic. This intra-tissue concentration should be maintained if possible by the administration regime, including by continuous infusion, sustained release, topical application, or injection at empirically determined frequencies. The progress of this therapy is easily monitored by conventional assays.

EXAMPLES

Example 1

A study was conducted to assess the ability of IL-12 administration to protect, or rescue, a mammal from lethal ionizing radiation and the results are presented in FIG. 1. Mice received recombinant murine IL-12 (100 ng/mouse (which is about 5 ug/kg on average), intravenous injection) before (24 hours) or after (1 hour) lethal dose radiation (1000 rad). Mice in control group received equal volume of PBS buffer. Survival rate were analyzed by Kaplan-Meier method and p value was calculated using Log Rank Test. The survival difference between IL-12 treatment (▲, n=38 or A, n=35) and control (⊟, n=62) is statistically significant (p<0.001). The survival difference between mice who received IL-12 before (▲) radiation and the control (⊟, n=62), and the survival difference between mice who received IL-12 after (△) radiation and the control (⊟, n=62) are also both statistically significant (p<0.05).

Example 2

A study was conducted to assess a low dose IL-12 can effectively protect a mammal from lethal dose ionizing radiation. To determine the minimum effective radioprotective dose of IL-12, different dose of IL-112 were administered to lethally irradiated animals before (24 hours before) or post (within one hour) lethal dose ionizing radiation. The best survival rate was obtained at dose of 5 ug/kg, in both before and post radiation administration. Higher dose (up to 50 ug/kg) did not yield greater survival. The dose of 5 ug/Kg can be converted to approximately 400 ng/kg as the appropriate human dose, using the general rule where the human dose is 1/12 of the murine dose. As shown in FIG. 1, when administrated at 100 ng/mouse (5 ug/Kg), 95% (administrated 24 hours before radiation) and 75% (administrated post radiation) animals showed long-term survival (more than one year) respectively, while all the control animals died within 24 days after receiving lethal dose radiation. IL-12 treated animals showed significant better survival (p<0.001) as compared with animals in control group. Interestingly, the difference before the animals received IL-12 before radiation and animals received IL-12 after radiation as compared with the control is also significant (p<0.05).

Example 3

IL-12 was administrated to mice at different doses 24 hours before radiation to determine if there is a dose dependent relationship between the concentration of IL-12 administration and survival from lethal irradiation. As shown in the Table 2, the optimal radioprotective dose in mice is about 100 ng/mouse or 5 ug/kg. This dose can be converted to about 400 ng/kg in humans (as the human dose is generally 1/12 of the murine dose).

TABLE 2

Radioprotection of IL-12 is dose dependent

| IL-12 dose (ng/mouse) | Total mice | Survives (30 days) | Survival rate (%) |
| --- | --- | --- | --- |
| 0 | 5 | 0 | 0 |
| 5 | 5 | 0 | 0 |
| 10 | 5 | 0 | 0 |
| 25 | 5 | 2 | 40 |
| 50 | 5 | 3 | 60 |
| 100 | 5 | 4 | 80 |
| 200 | 5 | 3 | 60 |

IL-12 was administrated at different dose 24 hours before radiation. As shown in the table, the optimal radioprotective dose is 100 ng/mosue.

Example 4

To further explore the relationship of IL-12 hematopoietic rescue effect as it may relate to the time of administration, IL-12 was administrated to lethally irradiated animals at different time before and after the radiation. The following time points were tested: −48, −36, −24, and −12 hours before radiation, or +1, +12, +24, and +36 hours post radiation. As shown in Table 3, when IL-12 administrated before radiation, the best results come from at −24 hours with all the animals survived (10 out of 10); while given post radiation, +1 hour gives the best rescue (4 out of 5 mice survived). Other injection time showed no (0% survival rate at −48, −36, +12 and +36 hours injection time for tested 5 animals in each group) or little (20% survival rate at −12 and +24 hours injection time for tested 5 animals).

TABLE 3

Radioprotective effects of IL-12 is injection-time dependent

| | control | Injection time before IR (hrs) | | | | Injection time after IR (hrs) | | | |
| --- | --- | --- | --- | --- | --- | --- | --- | --- | --- |
| | | 48 | 36 | 24 | 12 | 1 | 12 | 24 | 36 |
| Total mice | 10 | 10 | 10 | 10 | 10 | 5 | 5 | 10 | 5 |
| Survives | 0 | 0 | 0 | 10 | 2 | 4 | 0 | 2 | 0 |
| Survival rate (%) | 0 | 0 | 0 | 100 | 20 | 80 | 0 | 20 | 0 |

IL-12 administrated at different time before or post lethal dose radiation and the survival of the animals were observed daily. As shown in table 2, the best administration time for radioprotection is 24 hours before or 1 hour post radiation.
IR: lethal irradiation Example 5

A study was conducted to determine if the radioprotective effect of IL-12 administration is specific and INF-γ independent. To elucidate if this radioprotective effect is a common property of IL-12-related cytokines or if the radioprotective effect is IL-12 specific, the following cytokines were tested in the radioprotection assay: 1) IL-23, a heterodimer (p19+p40), which shares the same subunit p40 with IL-12 (p35+p40); IL-23 also shares the same receptor subunit, namely IL-12Rb, with IL-12; moreover, similar IL-12, the binding of IL-23 with its receptor result INF-γ production; 2) IL-18, like IL-12, can induce the release of interferon γ; 3) IL-2, which can synergistically function with IL-12 in immune response and increases the expression of IL-12 receptor in T cells; 4) GM-CSF, a cytokine to stimulate G and M cell production. As shown in Table 4, IL-12 is the only cytokine tested that can protect mice from lethal dose radiation (4 out of 5 mice survived when IL-12 is administrated post radiation). Also, an assessment was made to determine if there was a synergistic effect between GM-CSF and IL-12. No synergistic effect was found. Thus, the radioprotective function of IL-12 is specific and is interferon γ independent.

TABLE 4

Radioprotective effects of different cytokines

|  | Total mice | Survives | Survival rate (%) |
|---|---|---|---|
| Control | 5 | 0 | 0 |
| IL-2 | 5 | 0 | 0 |
| IL-18 | 4 | 0 | 0 |
| IL-23 | 5 | 0 | 0 |
| GM-CSF | 4 | 0 | 0 |
| IL-12 | 5 | 4 | 80 |
| IL-12 + GM-CSF | 5 | 4 | 80 |

Different cytokines were administrated to mice 1 hour post lethal dose radiation. The survival rates were observed by checking the animal survival daily. Although both IL-18 and IL-23 can induce INF-γ production, there was no radioprotective effect from these cytokines. This results suggested the radioprotective effect was IL-12 specific and INF-γ independent. Since GM-CSF only did not show any radioprotective effect and nor additive effectwhen used with IL-12 together, IL-12 only is sufficient to protect the animals from lethal dose radiation.
*: IL: interleukin; GM-CSF: granulocyte-macrophage colony-stimulating factor Example 6

A study was conducted to determine the effects of IL-12 administration and radiation on bone marrow and the intestinal tract. The major question to be answered in this study is whether IL-12 can protect bone marrow from the harmful effects of radiation without sensitizing the intestinal tract. The conclusion of the study is that IL-12 protects bone marrow from ionizing radiation, but does not sensitize the intestinal tract to the ionizing radiation.

Figure 2:
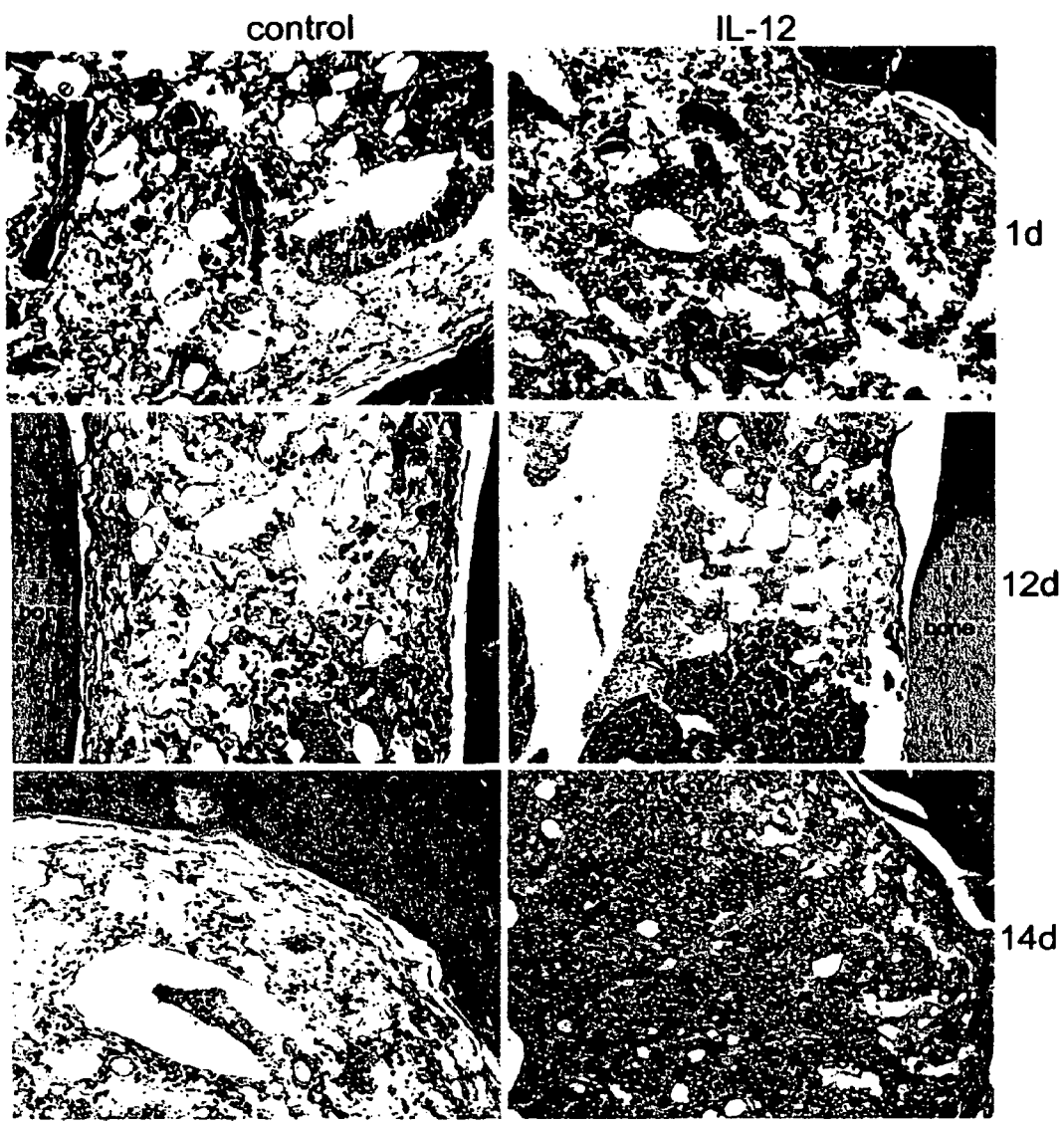
FIG. 2 shows that IL-12 administration protects bone marrow from lethal dose radiation in animal models. At different time post IL-12 treatment (5 ug/kg) and lethal dose radiation (1, 12 and 14 days), femurs were isolated, fixed in 10% formalin, decalcified and processed for paraffin section and for Hematoxylin & Eosin staining.
Figure 3:
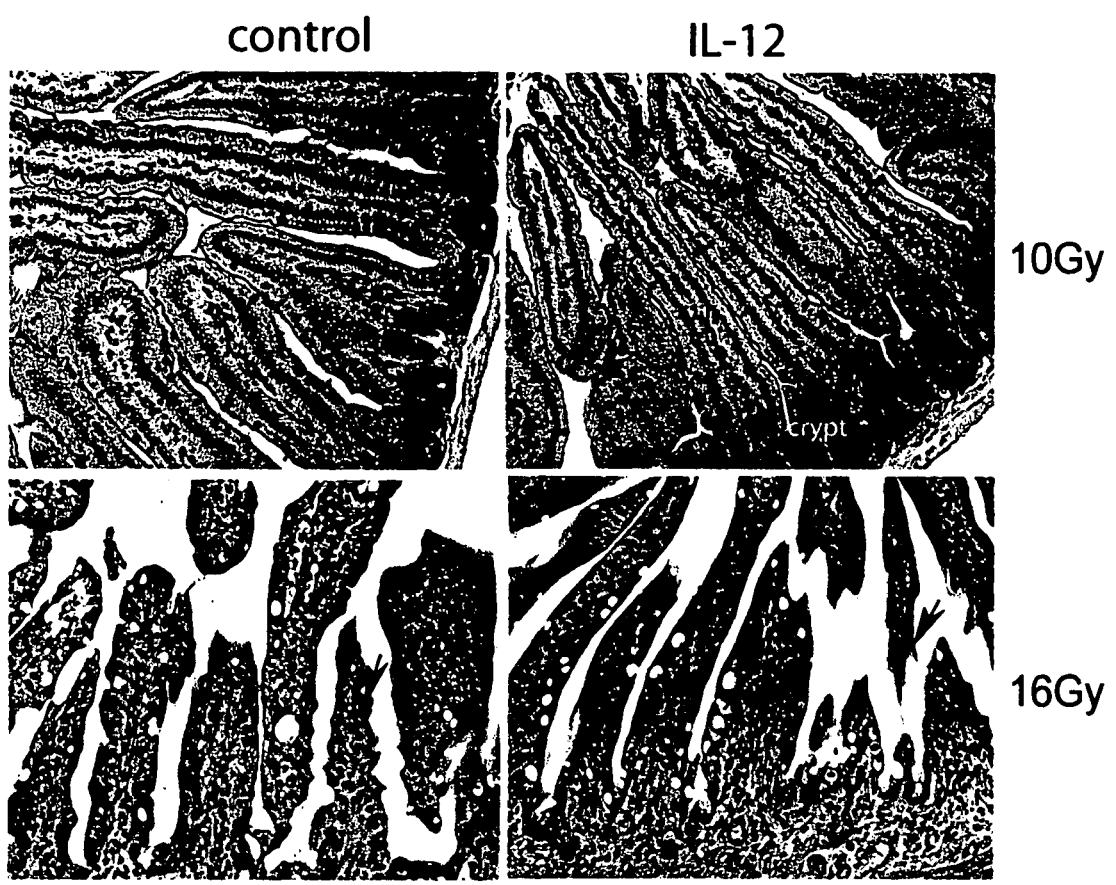
FIG. 3 show that low dose IL-12 (5 ug/kg) does not sensitize gastro-intestinal tract to two lethal dose radiation in animal models; IL-12 treated (5 ug/kg (approximately 10 ng/mouse)) or control mice received different dose radiation (10 and 16 Gy for bone marrow and GI tract lethal dose respectively). 4 days post radiation, small intestine were removed, fixed for PAS staining for mice received 10 Gy (Periodic Acid Schiff), H&E staining for mice received 16 Gy. There is no significant histological difference between control and IL-12 treated mice with both radiation dose. There is no obvious histological damage in mice who received 10 Gy radiation. (200× magnification)

To determine if IL-112 sensitizes intestinal tract to ionizing radiation, two different doses of IL-12 and radiation were used in radioprotection assay, namely 5 ug/kg and 50 ug/kg of IL-12 and two different doses of radiation were also used. Subsequent to the administration of IL-12 and radiation, both bone marrow and the small intestine were removed from mice who received either 5 ug/kg or 50 ug/kg of IL-12 and a lethal dose radiation for histology study. The lethal doses were either 1000 rad or 1600 rad. With 1000 rad, or 1600 rad), and a dose of 5 ug/kg IL-12, there is no significant difference for small intestine in control mice and IL-12 treated mice: the small intestine was intact in terms of shape and number of villa and crypt in the mice received 1000 rad radiation (FIG. 3), while there is lethal GI tract damage in the mice received 1600 rad radiation (mice both in control group and IL-12 treated group). However, bone marrow presented different profiles as shown in FIG. 2: Il-12 treated animals (5 ug/kg) showed protected marrow with significant higher cellularity at day 1 (control vs. IL-12 administration). There is no significant difference of bone marrow histological structure between mice in control and in IL-12 treated group at day 7 and day 10 post radiation (data not shown), though the bone marrow cellularity of IL-12 treated mice is better than control mice (data not shown). However, colonies were observed in IL-12 treated mice bone marrow at day 12 post radiation. By day 14, there is full recovery of bone marrow cellularity in IL-12 treated mice. Different from IL-12 treated group, the mice in control group did not show signs of bone marrow recovery all the time points studied.

Example 7

A study was conducted to show whether IL-12 administration promotes multi-lineage blood cell recovery from the effects of ionizing radiation. The peripheral blood cell counts drop is an index for damage of ionizing radiation on hematopoietic system. Since IL-12 demonstrated radioprotective effect from ionizing radiation, peripheral blood cell recovery was monitored in both lethal and sublethal dose radiation.

Figure 6:
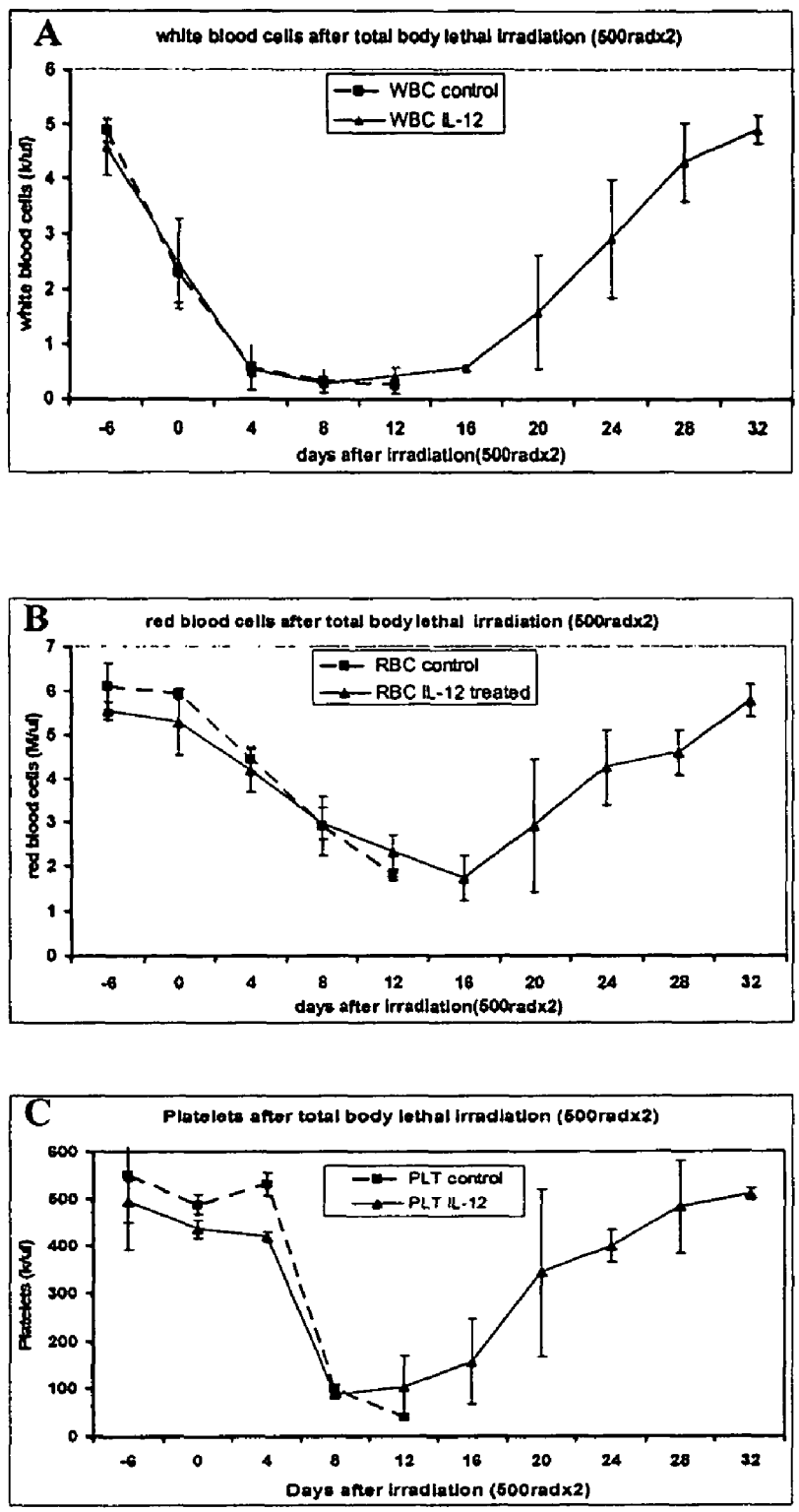
FIG. 6 shows that IL-12 administration promotes multiple lineage blood cell recovery of lethally irradiated mice; After IL-12 treatment (100 ng/mosue) and lethal dose radiation (10 Gy), peripheral blood were collected at different time via tail vein for blood cell counting and differentiation (Mascot from Brew).

After lethal dose radiation (10 Gy), the full blood cell count dropped to lowest point for both IL-12 treated and non-treated mice. However, 11-12 treated mice start to recover at day 14 post radiation while the control animals died out. The IL-12 treated animals reach to normal blood cell count at about 30 days post radiation, as shown in FIG. 6. It is noteworthy that the recovery is multi-lineage, including white blood cell, red blood cell and platelets. This result is expected to have significant clinical value as disclosed above.

Figure 4:
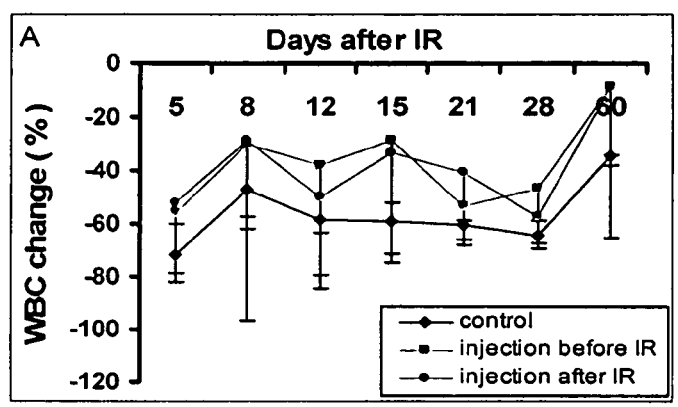
FIG. 4 shows that IL-12 administration promotes multiple lineage blood cell recovery of sublethally irradiated mice; After IL-12 treatment (100 ng/mosue) and sublethal radiation (500 rad), peripheral blood were collected at different time via tail vein for blood cell counting and differentiation (Mascot from Brew).
Figure 4B:
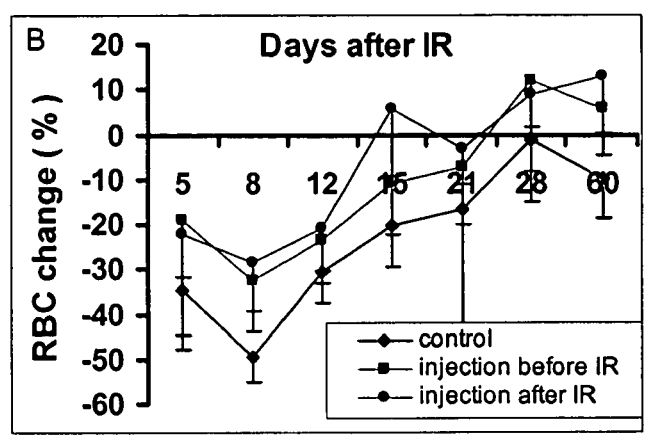
FIG. 4B: red blood cell count.
Figure 4C:
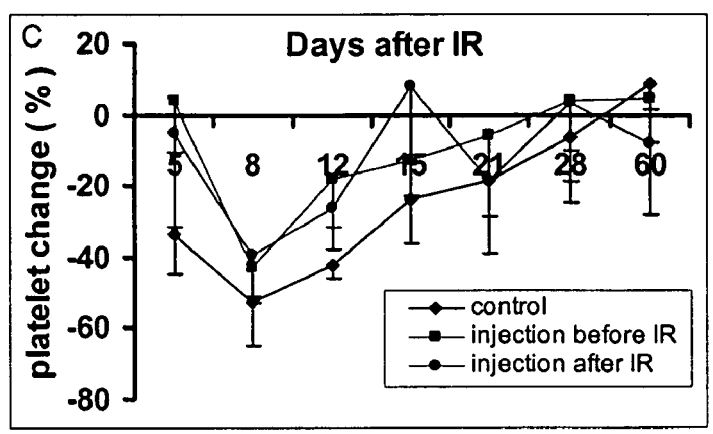
FIG. 4C: platelet count.
Figure 4D:
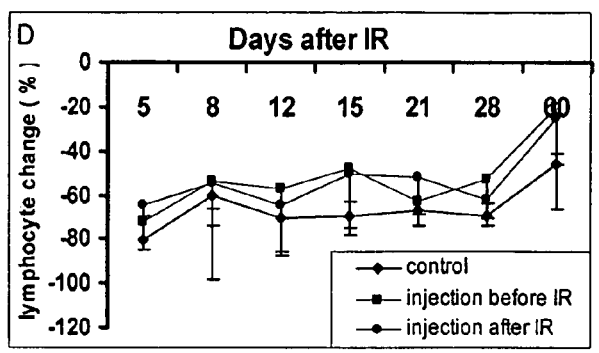
FIG. 4D: lymphocyte.
Figure 4E:
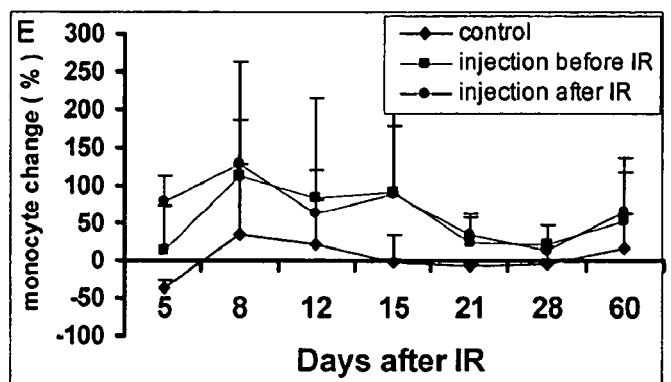
FIG. 4E: monocyte.
Figure 4F:
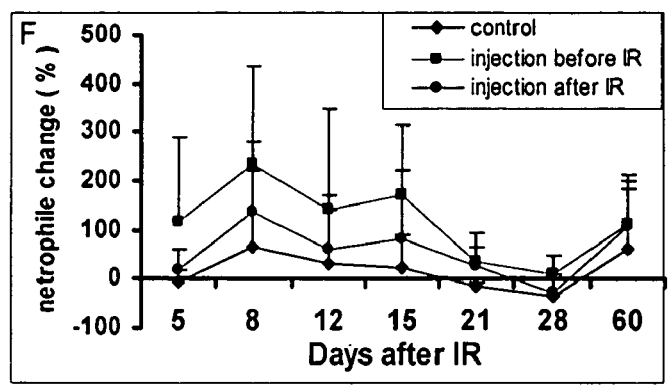
FIG. 4F: neurtrophile. Blue is the control while pink is IL-12 treatment 24 hours before irradiation and red is IL-12 treatment 1 hour after irradiation. IR: irradiation. p value for each subtype cell is under the figure and those p values less than 0.05 or 0.001 are in red color.

As shown in FIG. 4, sublethal radiation (500 rad), IL-12 accelerates the blood cell count recovery in treated mice as compared with control animals. Here too, the recovery is broad range and encompasses all blood lineages and blood cell types. Especially at day 5 and 8 post radiation, the red blood cell, platelet, white blood cell and monocyte from IL-12 treated mice are statistically higher as compared with control mice (p<0.05). This effect is somewhat better when IL-12 was administrated 24 hours before radiation than IL-12 administrated after radiation.

Example 8

Figure 5:
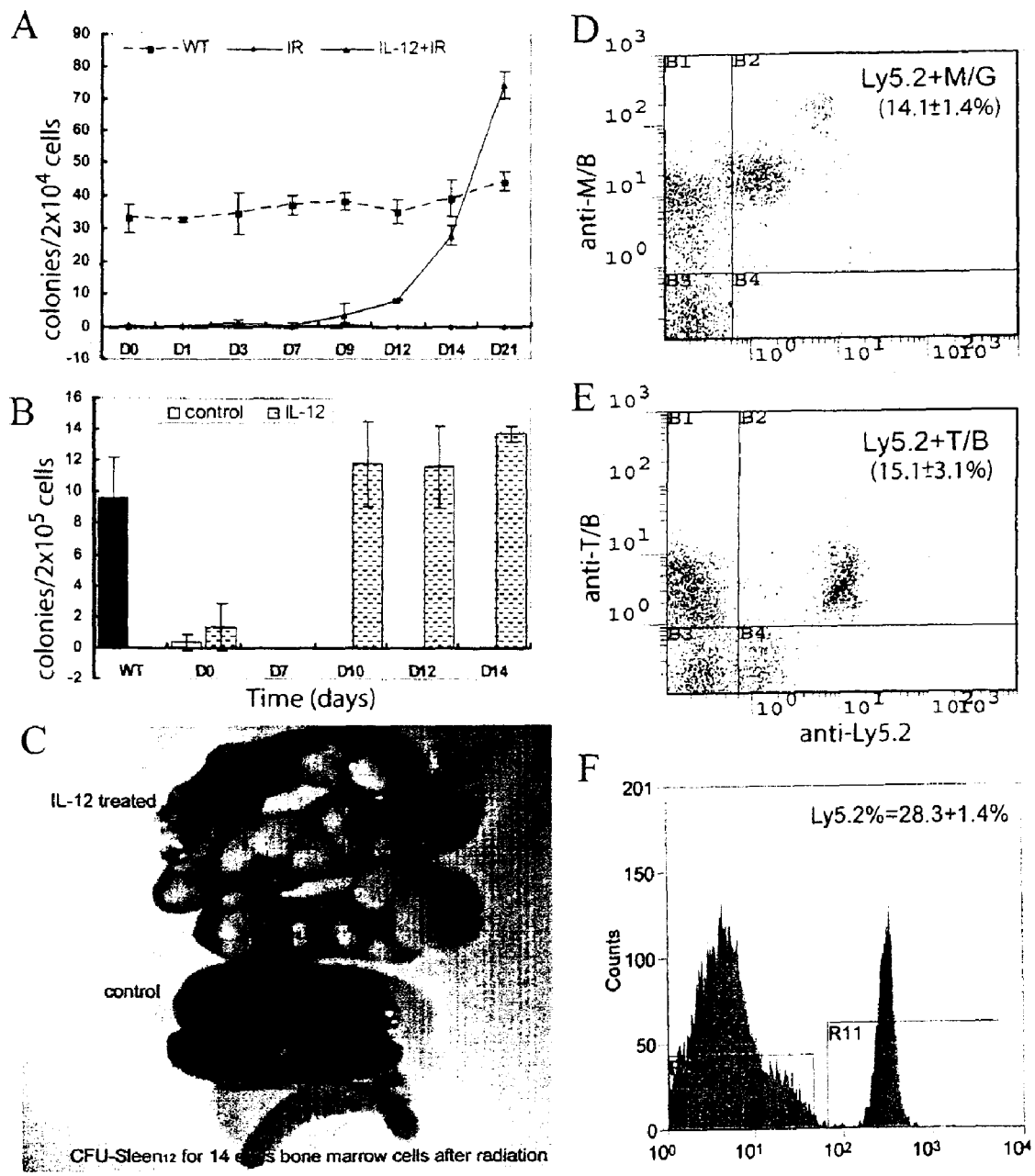
FIG. 5 IL-12 did not protect bone marrow progenitor cells or short-term hematopoietic stem cells (ST-HSCs) from lethal irradiation since there were no or little CFC (FIG. 5A) and CFU (FIG. 5B) activities in bone marrow cells immediately after or 7 days after irradiation. Till 10 days for CFU (FIGS. 5B&C) or 14 days for CFC (FIG. 5A) after irradiation, the colony-forming activities are almost fully recovered. These later CFU and CFC activities indicate they both were derived from protected long-term hematopoietic stem cells (LT-HSCs). The recovery for CFU (ST-HSCs) was about 4 days earlier than CFC (bone marrow progenitor cells). This matches with the normal bone marrow stem cells differentiation steps beginning from LT-HSC to ST-HSCs, then to more committed progenitor cells. Active LT-HSCs not only rescue lethally irradiated mice but also can completely repopulate the hematopoietic system. IL-12-protected LT-HSCs not only rescued the lethally irradiated mice and repopulated the hematopoietic system (FIG. 5F) but also differentiated into functional myeloid lineage (FIG. 5D) and lymphoid lineage (FIG. 5E) in long term. IL-12 administration protects long-term repopulating stem cells in lethally irradiated mice; At different time post lethal dose radiation, bone marrow cells were isolated from mice who received IL-12 or PBS buffer for colony forming cell assay (CFC assay) (FIG. 5A), colony forming units spleen day 12 assay (CFU-S12) (FIG. 5B-5C), and bone marrow transplantation (BMT, FIG. 5D-F); D: days after irradiation, D0: immediately after irradiation; IR, irradiation. BM, bone marrow. CFU-$S_{12}$, colony forming units—spleen12.

A study was conducted to assess whether IL-12 can protect progenitor cells in bone marrow from a lethal dose radiation
To determine the bone marrow cell subsets that are protected by IL-12 administration for the rescue phenomena, CFC and CFU-S$_{12}$ assay were performed at different time post lethal dose radiation. Bone marrow cells were recovered from IL-12 treated or control animals immediately (day 0), or at day 7, 9, 10, 12, 14 and 21 post radiation for CFC and CFU-S$_{12}$ assay. If progenitor cells are protected from IL-12 treatment (IL-12 was administered in this study at 24 hours before radiation), CFC and CFU-S$_{12}$ colonies should be detected when cells were removed at day 0. However, bone marrow cells isolated at day 0, 7 post radiation give rise no CFC nor CFU-S$_{12}$ colonies in both IL-12 treated and control animals. At day 10 post radiation, the bone marrow cells isolated from IL-12 treated mice start to give rise of CFU-S$_{12}$ but no detectable CFC, which start to appear from IL-112 treated bone marrow isolated 12 days post radiation and fully recovered from bone marrow cells isolated 14 days post radiation, as shown in FIGS. 5A and 5B. These results suggest that IL-12 does not directly protect bone marrow progenitor and short-term HSCs from lethal dose radiation. One explanation for this result is that there may be no CFC and CFU-S$_{12}$ colony forming cell left from lethal dose radiation in IL-12 treated animal bone marrow. The CFU-S$_{12}$ colony forming cells and CFC cells at day 10 and day 14 post radiation may be derived from long-term repopulating stem cells rescued by IL-12 treatment.

The experimental details are as follows. At different time post lethal dose radiation, bone marrow cells were isolated from mice who received IL-12 or PBS buffer for colony forming cell assay (CFC assay) (5A), colony forming units spleen day 12 assay (CFU-$S_{12}$) (5B-5C), and bone marrow transplantation (BMT, 5D-F). Legend: D0: immediately after irradiation; IR, irradiation. BM, bone marrow. CFU-$S_{12}$, colony forming units—spleen12.

FIG. 5A: Isolated bone marrow cells were plated in methycellulose plates for 12 days to detect colony formation. Bone marrow cells from normal mice were used as control for the assay system. There is no detectable CFC activity the first 9 days in both control and IL-12 treated mice. By day 12, there start to show low level CFC cell activity in IL-12 treated mice. The full recovery of CFC activity was observed at about 14 days post radiation in IL-12 treated mice. In contract, there is no recovery of CFC cell activity from control mice bone marrow cells.

FIG. 5B-C: Isolated bone marrow cells from IL-12 treated or control mice were transplanted to second lethally irradiated mice. 12 days post transplantation, the recipient mice were sacrificed and spleens were removed, fixed to count for colony formation. Cells isolated the first 7 days of both IL-12 treated and control mice did not give rise of CFU-$S_{12}$. However, a full recovered CFU-$S_{12}$ activity was observed from cells isolated 10 days post radiation in IL-12 treated mice. FIG. 5B shows the summary of 2 experiments with total of 6 mice; FIG. 5C shows the spleens isolated from mice received IL-12 or PBS buffer (control) bone marrow cells.

FIG. 5D-F: Secondary bone marrow transplantation was employed to detect if IL-12 can protect long-term repopulating HSC. Six month after lethal dose radiation and IL-12 rescue, bone marrow cells from these mice (Ly 5.2) were isolated and transplanted to secondary lethally irradiated mice (Ly 5.1). Four months after transplantation, donor cells (Ly5.2) were examined in recipient's peripheral blood. As shown in FIG. 5F, about 30% repopulated blood cells are of donor origin and donor cell derived T/B cell (FIG. 5E) and M/G (FIG. 5D) cell can be detected indicating that IL-12 protects long-term repopulating cells.

The following gives some further experimental details. Six months after the rescue from lethal dose radiation (IL-12 treated mice, C57BL/Ly5.2), whole bone marrow cells were isolated and 1×10⁶ cells were transplanted to secondary lethally irradiated mice (C57BL/Ly5.1). 4 months after transplantation, blood cells were collected and stained with anti-Ly5.2 and anti-Mac-1/anti-Gr-1antibodies (5D), and anti-Ly5.2 and anti-CD3/anti-B220 antibodies (5E) and anti-Ly5.2 antibody (5F). IL-12 rescued bone marrow cells gave rise to both myeloid lineage cells (5D, cells showed double positive of Ly5.2 and Mac-1/Gr-1 antigens); and lymphoid lineage cells (5E, cells showed double positive of Ly5.2 and CD3/B220 antigens). There were about 28±1% blood cells derived from IL-12 rescued bone marrow donor cells (5F). D: days after irradiation.

Example 9

A study was conducted to determine whether IL-12 administration stimulates bone marrow cell proliferation. The results of the study reveal that IL-12 promotes bone marrow cells into cycling and proliferation as compared with controls. It is believed that cells at S phase are more resistant to radiation. Both Brd-U incoperation and cell cycling analysis were performed to determine if IL-12 can stimulate bone marrow cell proliferation. In IL-12 treated mice, there are more bone marrow cells in S phase compared with control animals (12% vs 10%, p<0.05). Furthermore, there are more BrdU positive cells in IL-12 treated bone marrow compared with control animals (17% vs 8%, p<0.05).

Figure 7:
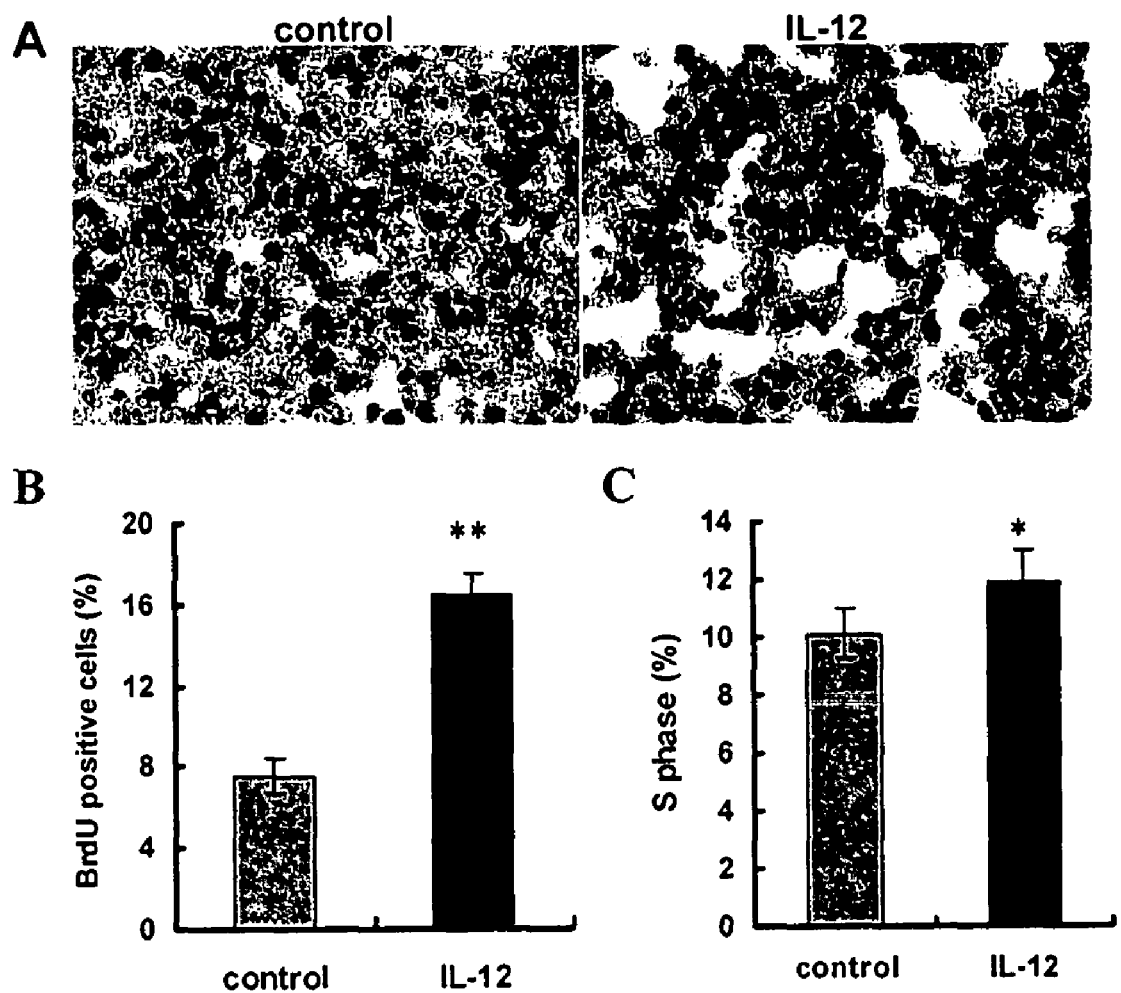
FIG. 7 shows that IL-12 administration generally stimulates bone marrow cell proliferation; 24 hours post IL-12 administration (10 ng/mouse), bone marrow cells were isolated for BrdU incooperation assay (FIG. 7A). Statistic analysis showed IL-12 treated bone marrow contains higher % of BrdU postitive cells compared with control mouse (B, $p<0.01$, n=6). Cell cycle analysis were performed with Propidium Iodide staining method which showed significant increased cell number at S phase (C, $p<0.05$, n=6).

These results are shown in FIG. 7. 24 hours post IL-12 administration (10 ng/mouse), bone marrow cells were isolated for BrdU incooperation assay (FIG. 7A). Statistical analysis showed IL-12 treated bone marrow contains higher levels of BrdU positive cells compared with control mouse (FIG. 7B, p<0.01, n=6). Cell cycle analysis were performed with Propidium Iodide staining method which showed significant increased cell number at S phase (C, p<0.05, n=6).

Example 10

Figure 8:
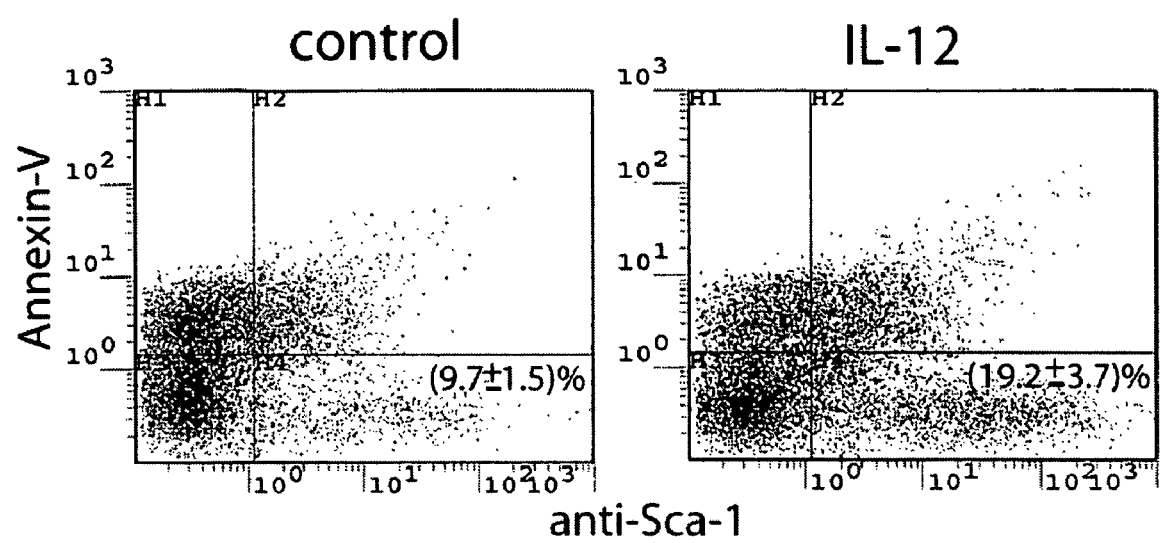
FIG. 8 IL-12 could significantly increase the percentage of Annexin V negative/Sca-1 positive cells (active bone marrow stem cells) in whole bone marrow compared with that of control (FIG. 8: $H_4$. 19.2±2.3% VS 9.7±1.5%, $p<0.01$) after irradiation. The proportion of Annexin V negative/Sca-1 positive cells in total Sca-1 positive cells (FIG. 8: $H_2+H_4$) was also significantly higher for IL-12 treatment than control (54±5% vs 44±5%, $p<0.05$). It indicated that there were more active bone marrow cells with stem markers (such as Sca-1) in IL-12 treated mice after lethal irradiation. IL-12 administration protects Annexin $V^-$/Sca-$1^+$ cells ($H_4$) from radiation induced apoptosis, where the Sca-$1^+$ positive cells are indicative of the presence of hematopoietic repopulating cell or hematopoietic stem cells and Annexin V negative cells are indicative of the functional bone marrow cells.

A study was conducted to assess whether IL-12 administration protects Sca-1+ cells from radiation induced apoptosis. The Sca-1+ is a marker for hematopoietic repopulating cell or stem/progenitor cells. 24 hours post IL-12 administration, mice received lethal dose radiation (10 Gy). 7 hours post radiation, mice were sacrificed and bone marrow cells were isolated to detect Annexin V (an indication of cell apoptosis) and Sca-1 antigen (stem cell marker). As shown in FIG. 8, compared with PBS treated control mice, the AnnexinV⁻ (negative for Annexin V)/Sca-1+ cells in IL-12 treated mice are significantly increased (19.2±3.7% vs 9.7±1.5%, p<0.01). The proportion of AnnexinV$^{-(negative)}$/Sca-1$^{+}$ cells in total Sca-1+ cells is significantly higher for IL-12 treated animals as compared with control mice (54±5% vs 44±5%, p<0.05).

Example 11

Figure 9A:
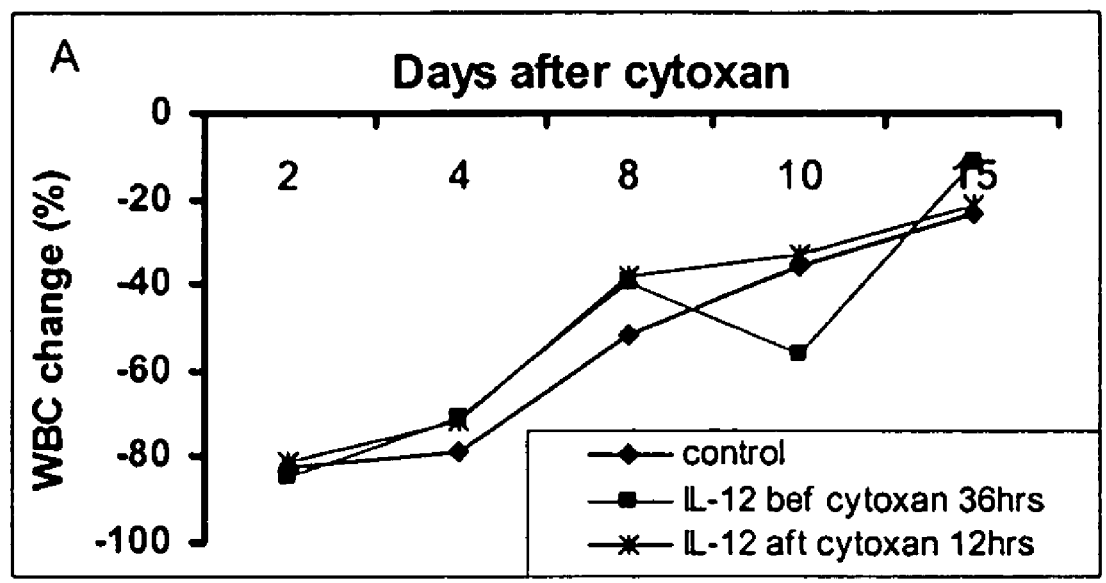
FIG. 9A: white blood cell.
Figure 9B:
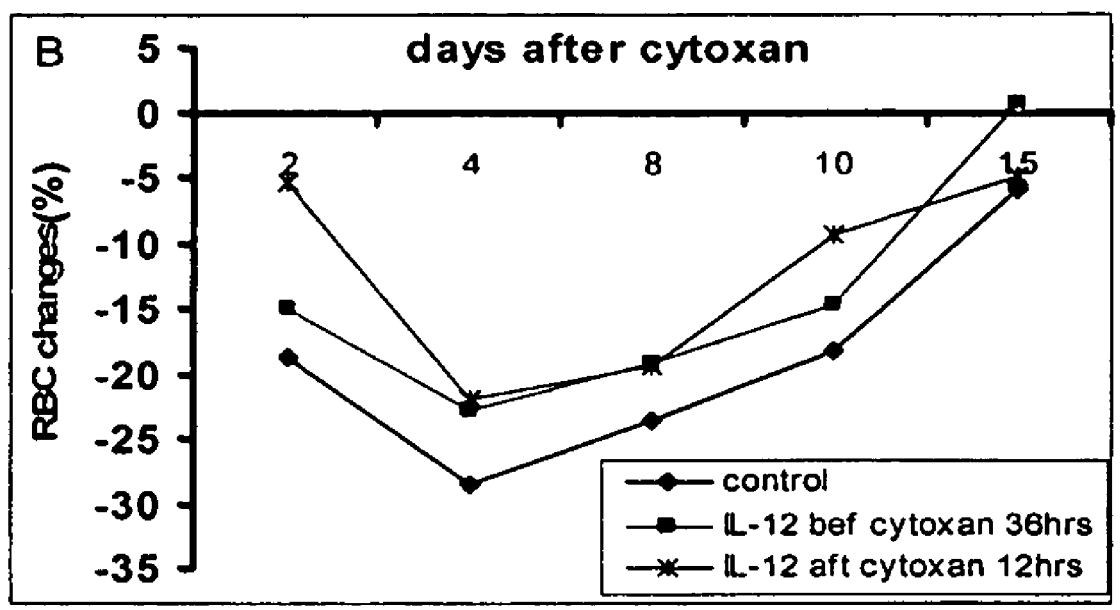
FIG. 9B: red blood cell.
Figure 9C:
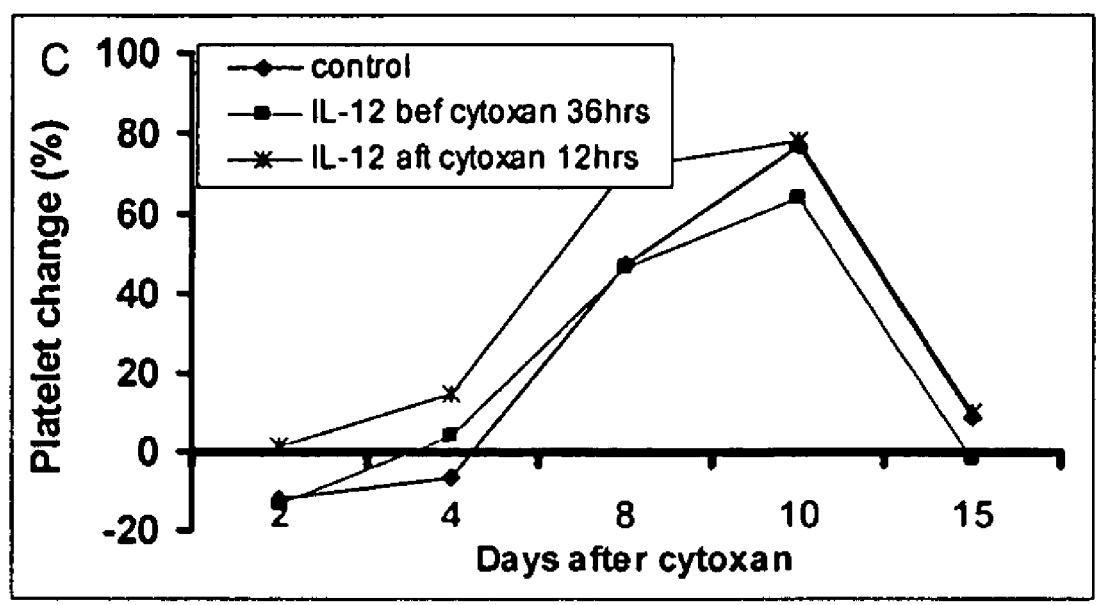
FIG. 9C: platelet.
Figure 9D:
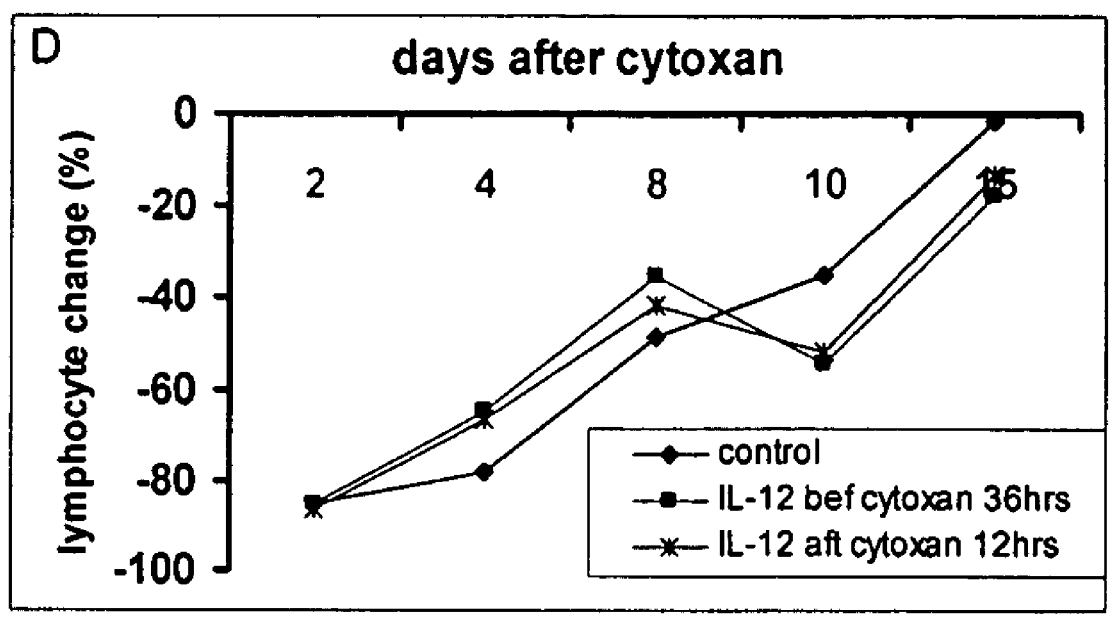
FIG. 9D: lymphocyte.
Figure 9E:
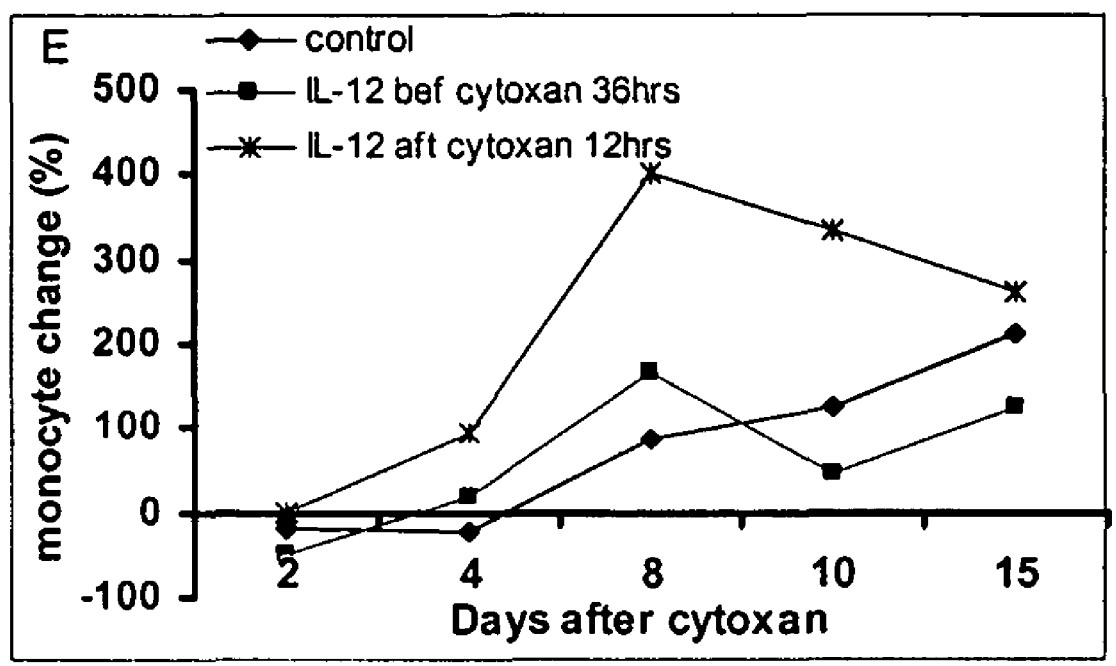
FIG. 9E: monocyte.
Figure 9F:
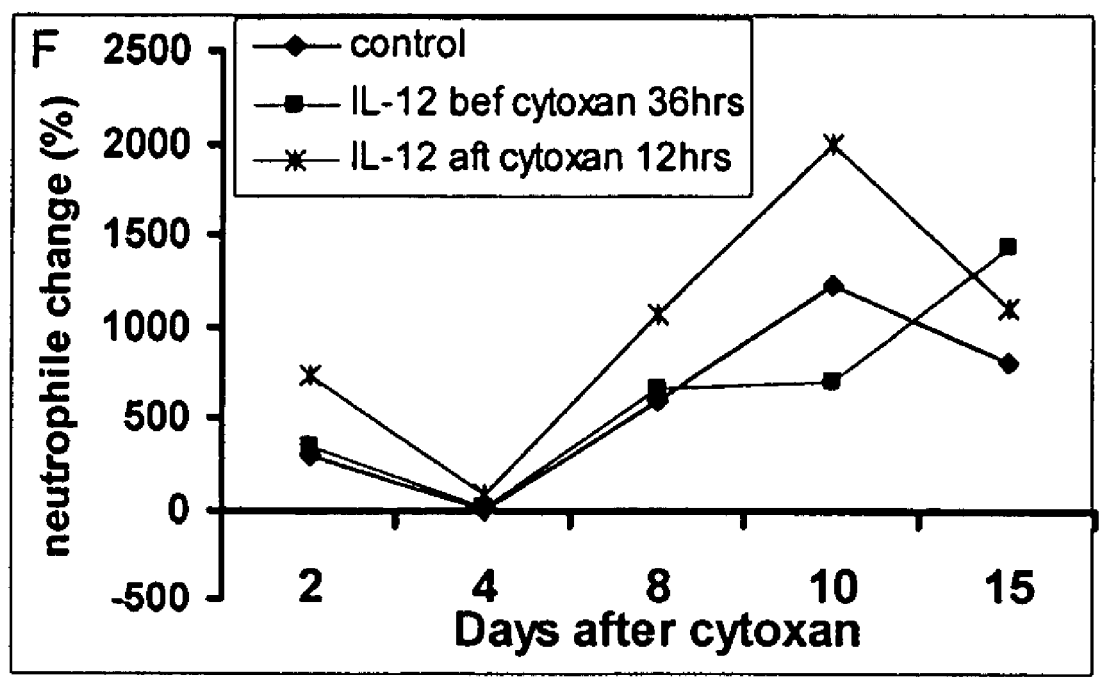
FIG. 9F: neutrophile. Cytoxan is name for cyclophosphamide.

A study was conducted to determine whether IL-12 administration promotes multi-lineage blood cell recovery when used in conjunction with a chemotherapeutic drug. In this example, use of IL-12 is as an adjuvant or ancillary therapy to the primary therapy of chemotherapy. IL-12 was administrated at different time (36 hrs before or 12 hrs after chemotherapy). Mice in this study received a relatively high dose of chemotherapeutic drug Cytoxan (e.g., 300 mg/kg). At different time post-cytoxan treatment, peripheral blood was collected via tail vein for blood cell count study. (Mascot). These datat are shown in FIG. 9. FIG. 9A white blood cell count; B: red blood cell count; C: platelet count. With limited mouse number (n=5), IL-12 treated mice showed better blood cell recovery.

Materials and Methods

Mice and Cytokines

All mice used in the above disclosed experiments were purchased from Jackson Labs (Bar Harbor, Me.). The specific mice used were C57BL/6J strain female mice were, generally 6 to 8 weeks old. Mice were handled and managed according to the protocol approved by the University of Southern California Animal Care and Use Committee. Recombinant murine interleukin 12 (IL-12) was purchased either from R&D Systems, Inc (Minneapolis, Minn.). or PeproTech Inc (Rocky Hill, N.J.) and was dissolved in phosphate buffered saline (PBS), pH 7.4 at 100 ng/ul stock concentration according to the manufacturer's recommendation, and stored at −70° C. Other cytokines or chemokines were bought from R&D Systems, Inc.

Radioprotection Assay

Mice were provided with acid water for one week before the radioprotection assay. Cytokines, diluted in phosphate buffered saline (PBS), pH 7.4, were intravenously injected into mice before or after total body lethal irradiation (TBI) at the specified times. Control group mice were injected with PBS buffer. For TBI, mice were either exposed twice to ionizing irradiation (γ-ray from Cesium 137) at 500 rad dose with a 3 hour interval, or one time at a dose of 1000 rad in a Gammacell 40 machine from Atomic Energy of Canada LTD (Kanafa, Ontario, Canada). The γ-ray exposure rate is 1 Gy/min. This radiation dose will cause all control group mice to die within 30 days after exposure. After irradiation, mice were given water containing antibiotics. For the survival curve, the Kaplan-Meier method was used. Each experiment was repeated three or more times.

For peripheral blood cell counts, 6-8 week old female C57BL/6J mice received an i.v. injection of IL-12 before or after lethal (1000 rad) or sub-lethal (500 rad) irradiation. 10 ul blood was taken from the tail to do blood cell count analyses in a MASCOT Multispecies Hematology Systems (CDC Technologies, Oxford, Conn.) at different days after irradiation. Each group had at least 3 mice.

Cell Cycling and Proliferation Assay

For the cell cycling assay, IL-12 (100 ng/mouse) or PBS was intravenously injected into mice. 24 hours after injection, whole bone marrow cells were flushed from femurs and treated with lysis buffer to destroy red blood cells. After washing in PBS and fixing in −20° C. pure ethanol for at least 1 hour, about $5 \times 10^5$ bone marrow cells were treated with RNase A (20 ng/ul final concentration) at 37° C. for 30 minutes, then stained with propidium iodide (100 ng/ul final concentration) from Sigma (St Louis, Mo.) at room temperature for 15 to 30 minutes and then processed directly for cell cycling analysis using fluorescence activated cell sorting (FACS).

For the BrdU assay, IL-12 (10 ng/mouse) or PBS was intravenously injected into mice. 21 hours after injection, mice were i.p. injected with 5-Bromo-2'-deoxyuridine (BrdU from Sigma) at 50 mg/kg dosage. 3 hours after BrdU injection, mice were sacrificed and whole bone marrow cells were isolated from femurs and treated with lysis buffer to destroy red blood cells. Bone marrow cells were dispersed on a slide by cytospin for the proliferation assay using BrdU immunohistochemistry system kit purchased from Oncogene Research Products (Boston, Mass.)

Pathology of Bone Marrow, Spleen and Small Intestine

Mice were treated with IL-12 (100 ng/mouse) or PBS 24 hours before receiving lethal irradiation. At different days after lethal irradiation, femurs, spleens and small intestines were removed and fixed in 10% formalin buffer for 24 hours. Subsequently, bone marrow was decalcified in Rapid Decalcifier for about 30 minutes. Samples and tissues then were embedded in TissuePrep 2 paraffin wax for micro-section at 5 μm for routine Hematoxylin and Eosin staining. Some small intestines were treated with PAS (Periodic Acid Schiff) staining.

IL-12 Radioprotective Effects on Long-Term Hematopoietic Stem Cells

Ly5.2 strain mice rescued by IL-112 treatment before or after lethal irradiation were sacrificed after 6 months. Whole bone marrow cells from these mice as donor cells ($1 \times 10^6$ Ly5.2 cells per recipient mouse or $5 \times 10^5$ Ly5.2 cells with $5 \times 10$ Ly5.1 competitor cells per recipient) were transplanted into Ly5.1 strain mice which received total body lethal irradiation. 4 months after the transplantation, peripheral blood cells were analyzed for Ly5.2 cells (anti-Ly5.2 antibody conjugated with FITC) with T cell and B cell markers (anti-CD3 and anti-B220 antibody conjugated with PE) and with macrophage and granulocyte cell markers (anti-CD11b and anti-Gr1 antibody conjugated with PE) using FACS. All antibodies were purchased from BD Pharmingen (San Diego, Calif.).

Colony-Forming Units (CFU) Assay and CFU-spleen$_{12}$ Assay 24 hours before lethal irradiation, mice were i.v. treated with IL-12 (100 ng/mouse) and bone marrow cells were isolated from these mice at different days after lethal irradiation. For CFU assay, $2 \times 10^5$ bone marrow cells were thoroughly mixed into 1 ml methylcellulose medium MethCult GF M3434 from StemCell Technologies Inc. (Vancouver, BC) and cultured into 35 mm dishes. Each sample was duplicated. After 12 days culture, colonies (>50 cells) were counted under microscope.

For the CFU-spleen1$_2$ assay, $2 \times 10^5$ bone marrow cells as donors were transplanted into recipient mice which received lethal irradiation. Cells from one donor mice were transplanted into three recipient mice. 12 days after transplantation, recipient mice were sacrificed and spleens were fixed in Tellyesniczky's solution (90 ml of 70% ethanol, 5 ml of glacial acetic acid, and 5 ml of 100% formalin). Spleen colonies were counted.

Although the present invention has been discussed in considerable detail with reference to certain preferred embodiments, other embodiments are possible. Therefore, the scope of the appended claims should not be limited to the description of preferred embodiments contained in this disclosure. All references and patents cited herein are incorporated by reference in their entirety.

What is claimed is:

1. A method for protecting or restoring hematopoiesis or enhancing peripheral blood cell counts in a mammal having at least one solid tumor, said method consisting essentially of:
    (a) administering a treatment to the mammal, wherein the treatment targets the solid tumor and has an associated hematopoietic toxicity; and
    (b) administering adjuvant therapy to alleviate the hematopoietic toxicity associated with said treatment, wherein the adjuvant therapy is selected from the group consisting of:
        (i) one therapeutically effective doses of IL-12 administered less than 36 hours before said treatment;
        (ii) one therapeutically effective dose of IL-12 administered at least 1 hour after said treatment; and
        (iii) one therapeutically effective dose of IL-12 administered less than 36 hours before said treatment and one therapeutically effective dose of IL-12 administered at least 1 hour after said treatment.

2. The method of claim 1, wherein the mammal is a human.

3. The method of claim 2, wherein each dose of IL-12 is between about 1 ng/kg and less than about 2000 ng/kg, and said dose is administered via a member selected from the group consisting of intradermal, intramuscular, intraperitoneal, intravenous, subcutaneous, and epidural routes.

4. The method of claim 2, wherein each dose of IL-12 is less than about 500 ng/kg.

5. The method of claim 2, wherein each dose of IL-12 is less than about 100 ng/kg.

6. The method of claim 2, wherein each dose of IL-12 is less than about 10 ng/kg.

7. The method of claim 1, wherein the treatment comprises chemotherapy.

8. The method of claim 7, wherein the chemotherapy leads to a deficiency in one or more hematopoietic cell types or lineages and the administration of IL-12 ameliorates the deficiency.

9. The method of claim 7, wherein the chemotherapy treatment comprises administration of more than one chemotherapy.

10. The method of claim 1, wherein the treatment comprises one or more high dose treatment modalities.

11. The method of claim 1, wherein the treatment is administered in a dose dense treatment regimen.

12. The method of claim 1, wherein the administration of IL-12 results in protection of bone marrow cells from the associated hematopoietic toxicity of the treatment.

13. The method of claim 12, wherein the bone marrow cells comprise hematopoietic repopulating cells, hematopoietic stem cells or hematopoietic progenitor cells.

14. The method of claim 1, wherein the method results in an increased remission of the one or more solid tumors, as compared with the treatment intended to target the solid tumor alone.

15. The method of claim 1, wherein IL-12 is administered by a method selected from the group consisting of:
 (a) less than 24 hours before said treatment,
 (b) at least 12 hours after said treatment, and
 (c) less than 24 hours before said treatment and at least 12 hours after said treatment.

* * * * *